United States Patent
Müller et al.

[11] Patent Number: 6,043,197
[45] Date of Patent: Mar. 28, 2000

[54] PYRIDYLACETIC ACID DERIVATIVES, PROCESS AND INTERMEDIATE PRODUCTS FOR THEIR PREPARATION AND THEIR USE

[75] Inventors: Bernd Müller, Frankenthal; Hubert Sauter; Herbert Bayer, both of Mannheim; Wassilios Grammenos, Ludwigshafen; Thomas Grote, Schifferstadt; Reinhard Kirstgen, Neustadt; Klaus Oberdorf, Heidelberg; Franz Röhl, Schifferstadt; Norbert Götz, Worms; Michael Rack, Heidelberg; Ruth Müller, Friedelsheim; Gisela Lorenz, Hambach; Eberhard Ammermann, Heppenheim; Siegfried Strathmann, Limburgerhof; Volker Harries, Frankenthal, all of Germany

[73] Assignee: BASF Aktiengesellschaft, Ludwigshafen, Germany

[21] Appl. No.: 09/051,895

[22] PCT Filed: Oct. 22, 1996

[86] PCT No.: PCT/EP96/04576

§ 371 Date: Apr. 23, 1998

§ 102(e) Date: Apr. 23, 1998

[87] PCT Pub. No.: WO97/16427

PCT Pub. Date: May 9, 1997

[30] Foreign Application Priority Data

Nov. 2, 1995 [DE] Germany .................. 195 40 734

[51] Int. Cl.[7] .................. A01N 43/40; C07D 213/54
[52] U.S. Cl. .................. 504/244; 546/332; 546/304; 546/290; 546/286
[58] Field of Search .................. 504/244, 254; 546/332, 286, 290, 304; 514/357

[56] References Cited

FOREIGN PATENT DOCUMENTS

| | | |
|---|---|---|
| 95/18789 | 7/1995 | WIPO . |
| 95/21153 | 8/1995 | WIPO . |
| 95/21154 | 8/1995 | WIPO . |
| 95/21156 | 8/1995 | WIPO . |

OTHER PUBLICATIONS

Patent Abstract of Japan, 08127563.

*Primary Examiner*—John Kight
*Assistant Examiner*—Charanjit S. Aulakh
*Attorney, Agent, or Firm*—Keil & Weinkauf

[57] ABSTRACT

Pyridylacetic acids of the formula I

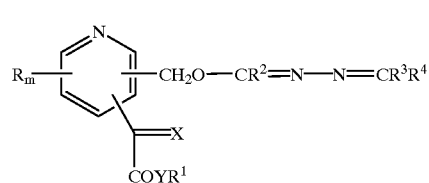

wherein

X is $NOCH_3$, $CHOCH_3$ and $CHCH_3$;

Y is oxygen or $NR^a$;

R is cyano, nitro, trifluoromethyl, halogen, alkyl and alkoxy;

m is 0, 1 or 2;

$R^1$ is hydrogen or alkyl;

$R^2$, $R^3$ and $R^4$ are hydrogen, cyano, nitro, hydroxyl, amino, halogen, unsubstituted or substituted alkyl, alkenyl, alkynyl, cycloalkyl, cycloalkenyl, heterocyclyl, aryl and hetaryl, each of which is bonded directly or via —O—, —S— or —N—, $R^4$ is furthermore $CR^d$=$NOR^e$;

or a salt thereof, processes and intermediates for their preparation and their use for controlling harmful fungi or pests.

10 Claims, No Drawings

PYRIDYLACETIC ACID DERIVATIVES, PROCESS AND INTERMEDIATE PRODUCTS FOR THEIR PREPARATION AND THEIR USE

This a U.S. national stage application under 35 U.S.C. §371 based on International Application No. PCT/EP 96/04,576, filed Oct. 22, 1996, now WO 97/18427 published May 9, 1997.

The present invention relates to pyridylacetic acid derivatives of the formula I

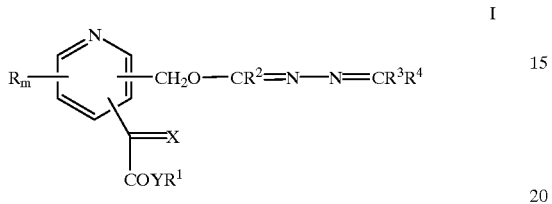

where the substituents and the index have the following meanings:

X is $NOCH_3$, $CHOCH_3$ and $CHCH_3$;

Y is oxygen or $NR^a$;

$R^a$ is hydrogen or $C_1$–$C_4$-alkyl;

R is cyano, nitro, trifluoromethyl, halogen, $C_1$–$C_4$-alkyl and $C_1$–$C_4$-alkoxy;

m is 0, 1 or 2, it being possible for the radicals R to be different when m is 2;

$R^1$ is hydrogen or $C_1$–$C_4$-alkyl;

$R^2$ and $R^3$ independently of one another are hydrogen, cyano, nitro, hydroxyl, amino, halogen, $C_1$–$C_6$-alkyl, $C_1$–$C_6$-alkoxy, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_2$–$C_6$-alkenylthio, $C_2$–$C_6$-alkenylamino, N-$C_2$–$C_6$-alkenyl-N-$C_1$–$C_6$-alkylamino, $C_2$–$C_6$-alkynyl, $C_2$–$C_6$-alkynyloxy, $C_2$–$C_6$-alkynylthio, $C_2$–$C_6$-alkynylamino, N-$C_2$–$C_6$-alkynyl-N-$C_1$–$C_6$-alkylamino, it being possible for the hydrocarbon radicals of these groups to be partially or fully halogenated or to have attached to them one to three of the following radicals: cyano, nitro, hydroxyl, mercapto, amino, carboxyl, aminocarbonyl, aminothiocarbonyl, halogen, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, aryl-$C_1$–$C_4$-alkoxy, arylthio, aryl-$C_1$–$C_4$-alkylthio, hetaryl, hetaryloxy, hetaryl-$C_1$–$C_4$-alkoxy, hetarylthio, hetaryl-$C_1$–$C_4$-alkylthio, it being possible for the cyclic radicals, in turn, to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and $C(=NOR^b)$—$A_n$—$R^c$;

$C_3$–$C_6$-cycloalkyl, $C_3$–$C_6$-cycloalkyloxy, $C_3$–$C_6$-cycloalkylthio, $C_3$–$C_6$-cycloalkylamino, N-$C_3$–$C_6$-cycloalkyl-N-$C_1$–$C_6$-alkylamino, $C_3$–$C_6$-cycloalkenyl, $C_3$–$C_6$-cycloalkenyloxy, $C_3$–$C_6$-cycloalkenylthio, $C_3$–$C_6$-cycloalkenylamino, N-$C_3$–$C_6$-cycloalkenyl-N-$C_1$–$C_6$-alkylamino, heterocyclyl, heterocyclyloxy, heterocyclylthio, heterocyclylamino, N-heterocyclyl-N-$C_1$–$C_6$-alkylamino, aryl, aryloxy, arylthio, arylamino, N-aryl-N-$C_1$–$C_6$-alkylamino, hetaryl, hetaryloxy, hetarylthio, hetarylamino, N-hetaryl-N-$C_1$–$C_6$-alkylamino, it being possible for the cyclic radicals to be partially or fully halogenated or to have attached to them one to three of the following groups: cyano, nitro, hydroxy, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkoxy-$C_1$–$C_6$-alkyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, di-$C_1$–$C_6$-alkylaminocarbonyl, $C_2$–$C_6$-alkenyl, $C_2$–$C_6$-alkenyloxy, benzyl, benzyloxy, aryl, aryloxy, aryl-$C_1$–$C_6$-alkoxy, hetaryl, hetaryloxy, it being possible for the cyclic radicals of the seven last-mentioned substituents to be partially or fully halogenated and/or to have attached to them a $C_1$–$C_6$-alkyl group; $C(=NOR^b)$—$A_n$—$R^c$ or $NR^f$—CO—D—$R^g$;

A is oxygen, sulfur or nitrogen, the nitrogen having attached to it hydrogen or $C_1$–$C_6$-alkyl;

D is a direct bond, oxygen or $NR^h$;

n is 0 or 1;

$R^b$, $R^c$ independently of one another are hydrogen or $C_1$–$C_6$-alkyl;

$R^f$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy and $C_1$–$C_6$-alkoxycarbonyl;

$R^g$, $R^h$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl;

$R^4$ is one of the groups mentioned under $R^2$ or a group $CR^d=NOR^3$;

$R^d$ is one of the groups mentioned under $R^2$;

$R^e$ is hydrogen, $C_1$–$C_{10}$-alkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_3$–$C_{10}$-alkynylcarbonyl or $C_1$–$C_{10}$-alkylsulfonyl, it being possible for these radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$- alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, $C_3$–$C_6$-cycloalkyl, $C_3$–$C_6$-cycloalkyloxy, heterocyclyl, heterocyclyloxy, benzyl, benzyloxy, aryl, aryloxy, arylthio, hetaryl, hetaryloxy and hetarylthio, it being possible fo the cyclic groups, in turn, to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or $C(=NOR^b)$—$A_n$—$R^c$;

$C_3$–$C_6$-cycloalkyl, aryl arylcarbonyl, arylsulfonyl, hetaryl, hetarylcarbonyl or hetarylsulfonyl, it being possible for these radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy, $C(=NOR^b)$—$A_n$—$R^c$ or $NR^f$—$CO$—$D$—$R^g$;

or a salt thereof.

Furthermore, the invention relates to processes and intermediates for the preparation of these compounds and to compositions comprising them for controlling animal pests and harmful fungi.

The literature discloses phenylacetic acid derivatives for controlling animal pests and harmful fungi (WO-A 95/18789, WO-A 95/21153, WO-A 95/21154, WO-A 95/21156).

It is an object of the present invention to provide compounds which have an improved activity.

We have found that this object is achieved by the phenylacetic acid derivatives I defined at the outset.

We have furthermore found processes and intermediates for their preparation, and compositions comprising them for controlling animal pests and harmful fungi and their use for this purpose.

The compounds I are obtainable by various routes by processes known per se from the literature.

When synthesizing the compounds I, it is, in principle, irrelevant whether the group —C(X)—COYR$^1$ or the group —CH$_2$OCR$^2$=N—N=CR$^3$R$^4$ is constructed first.

The construction of group —C(X)—COYR$^1$ is disclosed, for example, in the literature cited at the outset and in EP-A 178 826, EP-A 370 629, EP-A 422 597, EP-A 460 575, EP-A 463 488, EP-A 472 300, EP-A 493 711, EP-A 534 216, EP-A 658 541, EP-A 658 542, EP-A 658 543, WO-A 90/07493, WO-A 92/13830 and WO-A 92/18487.

The way in which the —CH$_2$OCR$^2$=N—N=CR$^3$R$^4$ side chain is synthesized depends essentially on the nature of the substituent R$^2$.

1. In the event that R$^2$ is not halogen, a procedure is generally followed when constructing the group CH$_2$COR$^2$=N—N=CR$^3$R$^4$ in which a benzyl derivative of the formula II is reacted with a carbohydrazide of the formula III

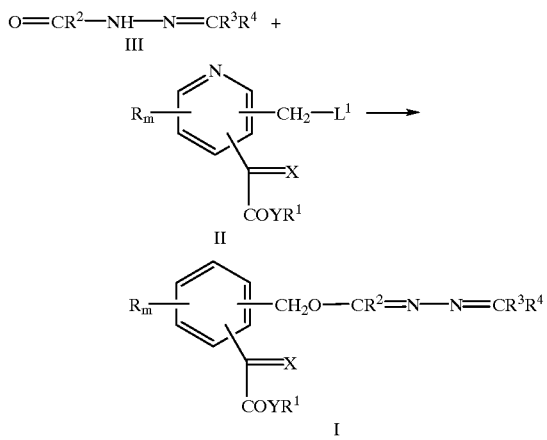

L$^1$ in formula II is a nucleophilically exchangeable leaving group, e.g., halogen or sulfonate groups, preferably chlorine, bromine, iodine, mesylate, tosylate or triflate.

The reaction is carried out in a manner known per se in an inert organic solvent in the presence of a base, e.g. sodium hydride, potassium hydroxide, potassium carbonate and triethylamine, by the methods described in Houben-Weyl, Vol. E 14b, p. 370 et seq. and Houben-Weyl, Vol. 10/1, p. 1189 et seq.

The carbohydrazide III is obtained, for example, by processes known from the literature (e.g. Maquestian, *Tetrahedron* 1987, 4185; Houben-Weyl, *Methoden der organischen Chemie* [*Methods in Organic Chemistry*], *Register der Stoffklassen* [*Register of substance classes*] Part A, Vol. 16/2, pp. 439–454).

2. Compounds where R$^2$ is a halogen atom are obtained from the corresponding precursors where the radical in question is a hydroxyl group by methods known per se (cf. Houben-Weyl, Vol. E5, p. 631; J. Org. Chem. 36, 233 (1971); J. Org. Chem. 57, 3245 (1992).

3. Compounds where R$^2$ is bonded to the molecule skeleton via an O, S or N atom are obtained from the corresponding precursors in which the radical in question is a halogen atom by methods known per se (cf. Houben-Weyl, Vol. E5, p. 826 et seq. and 1280 et seq., J. Org. Chem. 36, 233 (1971), J. Org. Chem. 46, 3623 (1981)).

4. Compounds where R$^2$ bonded to the molecule via an oxygen atom are in some cases also obtained by methods known per se from the corresponding precursors where the radical in question is a hydroxyl group (cf. Houben-Weyl, Vol. E 5, pp. 826–829, Aust. J. Chem. 27, 1341–9 (1974)).

5. In a preferred process, the compounds I where Y is oxygen are obtained by converting the aldehyde IV into the cyanohydrin V by methods similar to those described in EP-A 493 711 and EP-A 534 216, reacting V by the methods of a Pinner reaction to give the hydroxyester VI, oxidizing VI to the ketoester VII and converting VII either a) with O-methylhydroxylamine or an O-methylhydroxylammonium salt, b) with an ethylene Wittig or ethylene Wittig Horner reagent, or c) with a methoxy Wittig or methoxy Wittig Horner reagent into the pyridine VIII, subsequently reacting VIII to give the halogen derivative IIa, b or c (Hal=Cl, Br) and converting IIa, b or c into Ia, b or c using a nucleophile III.

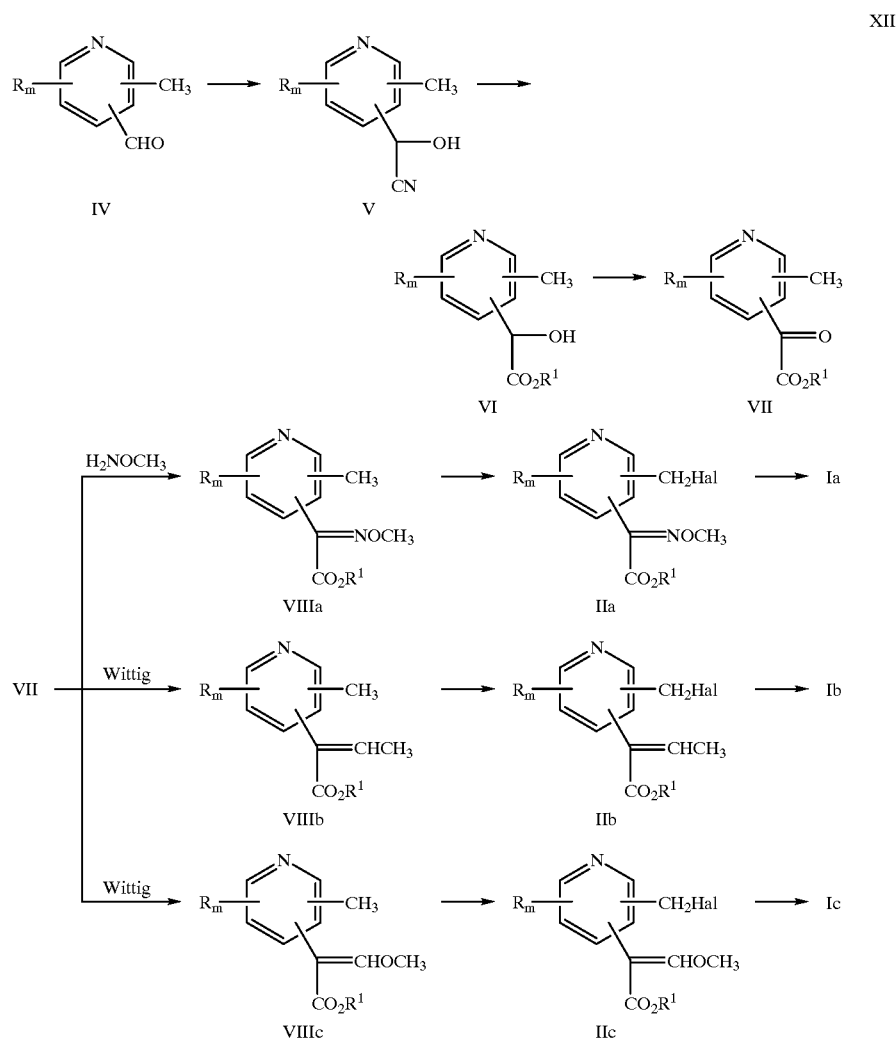

6. In a further preferred process, the intermediates IIa, b or c are obtained by carrying out the synthesis described under item 5., but starting from protected derivatives IX.

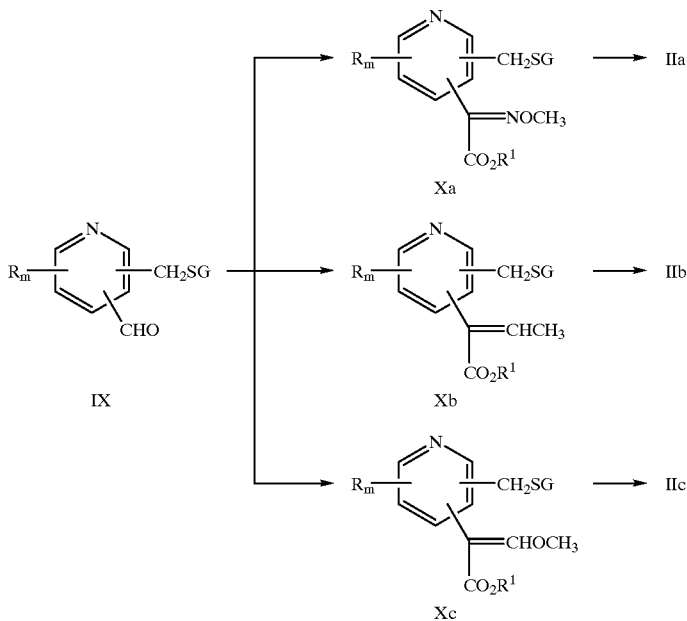

In the compounds IX and X, SG is a protective group which can be eliminated under acidic conditions, such as alkoxy, aryloxy and acyloxy. The elimination is carried out by the methods described in the literature [cf. T. W. Greene, *Protective Groups in Organic Synthesis*, John Wiley & Sons 1981], for example using HBr, HCl or BBr$_3$.

7. Compounds of the formula I where Y is NR$^a$ are obtained from the corresponding compounds Ia in a manner known per se by reacting them with an amine of the formula VI.

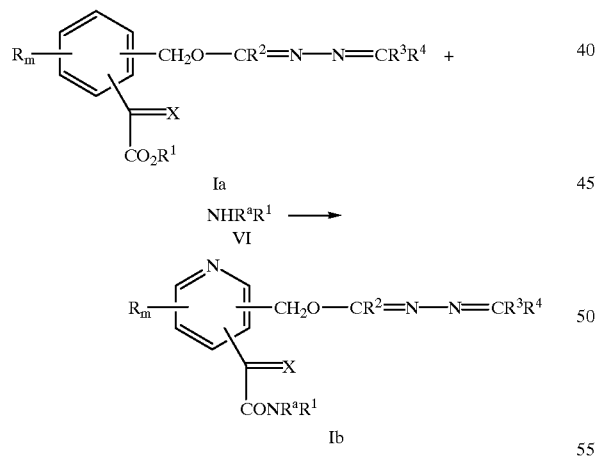

The reaction of the ester Ia with the amine is usually carried out at from 0° to 80° C., preferably 15° C. to 60° C. [cf. EP-A 543 216].

Suitable solvent are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide and dimethylformamide, especially preferably water, methanol, acetonitrile and tert-butyl methyl ether. Mixtures of these can also be used.

Suitable bases are, generally, inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides such as lithium hydride, sodium hydride, potassium hydride and calcium hydride, alkali metal amides such as lithium amide, sodium amide and potassium amide, alkali metal carbonates and alkaline earth metal carbonates such as lithium carbonate and calcium carbonate, and alkali metal hydrogen carbonates such as sodium hydrogen carbonate, organometal compounds, in particular alkali metal alkyls such as methyllithium, butyllithium and phenyllithium, alkylmagnesium halides such as methylmagnesium chloride, and alkali metal alcoholates and alkaline earth metal alcoholates such as sodium methanolate, sodium ethanolate, potassium ethanolate, potassium tert-butanolate and dimethoxymagnesium, furthermore organic bases, e.g. tertiary amines such as trimethylamine, triethylamine, triisopropylethylene and n-methylpiperidine, pyridine, substituted pyridines such as collidine, lutidine and 4-dimethylaminopyridine, and bicyclic amines.

In general, the bases are employed in catalytic amounts, but they can also be used in equimolar amounts, in an excess or, if desired as the solvent.

In general, the starting materials are reacted with each other in equimolar amounts. It may be advantageous for the yield to employ an excess of the amine HNR$^a$R$^1$ based on Ia.

Those compounds III which are not already known can be prepared by conventional methods.

The reaction mixtures are worked up in a customary manner, e.g. by mixing with water, phase separation and, if desired, chromatographic purification of the crude products. Some of the intermediates and end products are obtained in the form of colorless or pale brown viscous oils which are freed, or purified, from volatile components under reduced pressure and at moderately elevated temperatures. If the intermediates and end products are obtained as solids, they may also be purified by recrystallization or digestion.

When preparing the compounds I, they may be obtained, due to their C=C and C=N double bonds, in the form of E/Z isomer mixtures which can be resolved into the single compounds in the customary manner, e.g. by crystallization or chromatography.

If isomer mixtures are obtained from the synthesis, a separation is, however, generally not absolutely necessary since in some cases the individual isomers can be converted into each other during formulation for use or upon use (e.g. when exposed to light, acids or bases). Such conversions can also take place after use, in the treatment of plants for example in the treated plant, or in the harmful fungus or animal pest to be controlled.

Regarding their activity, the E isomers of the compounds I, based on the C=X double bond, are preferred (configuration baed on the $OCH_3$ or $CH_3$ group relative to the $COYR^1$ group).

Regarding their activity, the cis isomers of the compounds I, based on the $—CR^2=N—N=CR^3R^4$ double bonds (configuration based on the radical $R^2$ relative to the $—N=CR^3R^4$ group, or based on the radical $R^3$ relative to the $—N=CR^2—$ group), are preferred.

In the definitions of the compounds I given at the outset, collective terms were used which generally represent the following groups:

halogen: fluorine, chlorine, bromine and iodine;

alkyl: straight-chain or branched alkyl groups having 1 to 4, 6 or 10 carbon atoms, e.g. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

alkylamino: an amino group which has attached to it a straight-chain or branched alkyl group having 1 to 6 carbon atoms as mentioned above;

dialkylamino: an amino group which has attached to it two straight-chain or branched alkyl groups, independent of one another and having in each case 1 to 6 carbon atoms as mentioned above;

alkylcarbonyl: straight-chain or branched alkyl groups having 1 to 10 carbon atoms which are bonded to the skeleton via a carbonyl group (—CO—);

alkylsulfonyl: straight-chain or branched alkyl groups having 1 to 6 or 10 carbon atoms which are bonded to the skeleton via a sulfonyl group (—$SO_2$—);

alkylsulfoxyl: straight-chain or branched alkyl groups having 1 to 6 carbon atoms which are bonded to the skeleton via a sulfoxyl group (—S(=O)—);

alkylaminocarbonyl: alkylamino groups having 1 to 6 carbon atoms as mentioned above which are bonded to the skeleton via a carbonyl group (—CO—);

dialkylaminocarbonyl: dialkylamino groups having in each case 1 to 6 carbon atoms per alkyl radical as mentioned above which are bonded to the skeleton via a carbonyl group (—CO—);

alkylaminothiocarbonyl: alkylamino groups having 1 to 6 carbon atoms as mentioned above which are bonded to the skeleton via a thiocarbonyl group (—CS—);

dialkylaminothiocarbonyl: dialkylamino groups having in each case 1 to 6 carbon atoms per alkyl radical as mentioned above which are bonded to the skeleton via a thiocarbonyl group (—CS—);

haloalkyl: straight-chain or branched alkyl groups having 1 to 6 carbon atoms, it being possible for some or all of the hydrogen atoms in these groups to be replaced by halogen atoms as mentioned above, e.g. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups having 1 to 4 or 6 carbon atoms as mentioned above which are bonded to the skeleton via an oxygen atom (—O—), e.g. $C_1$–$C_6$-alkoxy such as methyloxy, ethyloxy, propyloxy, 1-methylethyloxy, butyloxy, 1-methylpropyloxy, 2-methylpropyloxy, 1,1-dimethylethyloxy, pentyloxy, 1-methylbutyloxy, 2-methylbutyloxy, 3-methylbutyloxy, 2,2-dimethylpropyloxy, 1-ethylpropyloxy, hexyloxy, 1,1-dimethylpropyloxy, 1,2-dimethylpropyloxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropyloxy, 1,2,2-trimethylpropyloxy, 1-ethyl-1-methylpropyloxy and 1-ethyl-2-methylpropyloxy;

alkoxycarbonyl: straight-chain or branched alkyl groups having 1 to 6 carbon atoms which are bonded to the skeleton via an oxycarbonyl group (—CO(=O)—);

haloalkoxy: straight-chain or branched alkyl groups having 1 to 6 carbon atoms, it being possible for some or all of the hydrogen atoms in these groups to be replaced by halogen atoms as mentioned above, and these groups being bonded to the skeleton via an oxygen atom;

alkylthio: straight-chain or branched alkyl groups having 1 to 4 or 6 carbon atoms as mentioned above which are bonded to the skeleton via a sulfur atom (—S—), e.g. $C_1$–$C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

cycloalkyl: monocylic alkyl groups having 3 to 6 carbon ring members, e.g. cyclopropyl, cyclobutyl, cyclopentyl and cyclohexyl;

alkenyl: straight-chain or branched alkenyl groups having 2 to 6 or 10 carbon atoms and one double bond in any position, e.g. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-di-methyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkenyloxy: straight-chain or branched alkenyl groups having 2 to 6 carbon atoms and one double bond in any position which are bonded to the skeleton via an oxygen atom (—O—);

alkenylthio or alkenylamino: straight-chain or branched alkenyl groups having 2 to 6 carbon atoms and one double bond in any position which are bonded to the skeleton via a sulfur atom (alkenylthio) or via a nitrogen atom (alkenylamino);

alkenylcarbonyl: straight-chain or branched alkenyl groups having 2 to 10 carbon atoms and one double bond in any position which are bonded to the skeleton via a carbonyl group (—CO—);

alkynyl: straight-chain or branched alkynyl groups having 2 to 10 carbon atoms and one triple bond in any position, e.g. $C_2$–$C_6$-alkynyl such as ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

alkynyloxy or alkynylthio and alkynylamino: straight-chain or branched alkynyl groups having 2 to 6 carbon atoms and one triple bond in any position which are bonded to the skeleton via an oxygen atom (alkynyloxy) or a sulfur atom (alkynylthio) or a nitrogen atom (alkynylamino);

alkynylcarbonyl: straight-chain or branched alkynyl groups having 3 to 10 carbon atoms and one triple bond in any position which are bonded to the skeleton via a carbonyl group (—CO—);

cycloalkenyl, or cycloalkenyloxy, cycloalkenylthio and cycloalkenylamino: monocyclic alkenyl groups having 3 to 6 carbon ring members which are bonded to the skeleton directly, or via an oxygen atom (cycloalkenyloxy) or a sulfur atom (cycloalkenylthio) or a nitrogen atom (cycloalkenylamino), e.g., cyclobutenyl, cyclopentenyl or cyclohexenyl.

cycloalkoxy, or cycloalkylthio and cycloalkylamino: monocyclic alkenyl groups having 3 to 6 carbon ring members which are bonded to the skeleton via an oxygen atom (cycloalkyloxy) or a sulfur atom (cycloalkylthio) or a nitrogen atom (cycloalkylamino), e.g. cyclopropyl, cyclobutyl, cyclopentyl or cyclohexyl;

heterocyclyl, or heterocyclyloxy, heterocyclylthio and heterocyclylamino: three- to six-membered saturated or partially unsaturated mono- or polycyclic heterocycles which contain one to three hetero atoms selected from a group consisting of oxygen, nitrogen and sulfur, and which are bonded to the skeleton directly, or via an oxygen atom (heterocyclyloxy) or via a sulfur atom (heterocyclylthio) or via a nitrogen atom (heterocyclylamino), e.g. 2-tetrahydrofuranyl, oxiranyl, 3-tetrahydrofuranyl, 2-tetrahydrothienyl, 3-tetrahydrothienyl, 2-pyrrolidinyl, 3-pyrrolidinyl, 3-isoxazoldinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 5-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-thiazolidin-3-yl, 1,2,4-triazolidin-5-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydrofur-4-yl, 2,3-dihydrofur-5-yl, 2,5-dihydrofur-2-yl, 2,5-dihydrofur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,3-dihydroisothiazol-3-yl, 2,3-dihydroisothiazol-4-yl, 2,3-dihydroisothiazol-5-yl, 4,5-dihydroisothiazol-3-yl, 4,5-dihydroisothiazol-4-yl, 4,5-dihydroisothiazol-5-yl, 2,3-dihydropyrazol-3-yl, 2,3-dihydropyrazol-4-yl, 2,3-dihydropyrazol-5-yl, 4,5-dihydropyrazol-3-yl, 4,5-dihydropyrazol-4-yl, 4,5-dihydropyrazol-5-yl, 2,5-dihydropyrazol-3-yl, 2,5-dihydropyrazol-4-yl, 2,5-dihydropyrazol-5-yl, 2,3-dihydrooxazol-2-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl;

aryl, or aryloxy, arylthio, arylcarbonyl and arylsulfonyl: aromatic mono- or polycyclic hydrocarbon radicals which are bonded to the skeleton directly, or via an oxygen atom (—O—; aryloxy) or a sulfur atom (—S—; arylthio), via a carbonyl group (—CO—; arylcarbonyl) or via a sulfonyl group (—SO$_2$—; arylsulfonyl), e.g., phenyl, naphthyl and phenanthrenyl, or phenyloxy, naphthyloxy and phenanthrenyloxy and the corresponding carbonyl and sulfonyl radicals;

arylamino: aromatic mono- or polycyclic hydrocarbon radicals which are bonded to the skeleton via a nitrogen atom;

hetaryl, or hetaryloxy, hetarylthio, hetarylcarbonyl and hetarylsulfonyl: aromatic mono- or polycyclic radicals which, besides carbon ring members, can additionally contain one to four nitrogen atoms or one to three nitrogen atoms and one oxygen or one sulfur atom or one oxygen or one sulfur atom and which are bonded to the skeleton directly, or via an oxygen atom (—O—; hetaryloxy) or a sulfur atom (—S—; hetarylthio), via a carbonyl group (—CO—; hetarylcarbonyl) or via a sulfonyl group (—SO$_2$—; hetarylsulfonyl), e.g.

5-membered hetaryl containing one to three nitrogen atoms: 5-membered hetaryl ring groups which, besides carbon ring members, can contain one to three nitrogen atoms as ring members, e.g. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered hetaryl containing one to four nitrogen atoms or one to three nitrogen atoms and one sulfur or oxygen atom or one oxygen or one sulfur atom: 5-membered hetaryl ring groups which, besides carbon ring atoms, can contain one to four nitrogen atoms or one to three nitrogen atoms and one sulfur or oxygen atom or one oxygen or sulfur atom as ring members, e.g. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,2,4-triazol-3-yl, 1,3,4-triazol-2-yl, 1,2,3,4-tetrazolyl;

benzo-fused 5-membered hetaryl, containing one to three nitrogen atoms or one nitrogen atom and/or one oxygen or sulfur atom: 5-membered hetaryl groups which, besides carbon atoms, can contain one to four nitrogen atoms or one to three nitrogen atoms and one sulfur or oxygen atom or one oxygen or one sulfur atom as ring members and in which two adjacent carbon ring members or one nitrogen and an adjacent carbon ring member can be bridged by a buta-1,3-diene-1,4-diyl group;

5-membered hetaryl, bonded via nitrogen and containing one to four nitrogen atoms, or benzo-fused 5-membered hetaryl, bonded via nitrogen and containing one to three nitrogen atoms: 5-membered hetaryl ring groups which, besides carbon atoms, can additionally contain one to four nitrogen atoms, or one to three nitrogen atoms, as ring members and in which two adjacent carbon ring members or one nitrogen and one adjacent carbon ring member can be bridged by a buta-1,3-diene-1,4-diyl group, these rings being bonded to the skeleton via one of the nitrogen ring members;

6-membered hetaryl containing one to three, or one to four, nitrogen atoms: 6-membered hetaryl ring groups which, besides carbon atoms, can contain one to three, or one to four, nitrogen atoms as ring members, e.g. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered hetaryl, containing one to four nitrogen atoms: 6-membered hetaryl ring groups in which two adjacent carbon ring members can be bridged by a buta-1,3-diene-1,4-diyl group, e.g. quinoline, isoquinoline, quinazoline and quinoxaline, and the corresponding oxy, thio, carbonyl or sulfonyl groups.

Hetarylamino: aromatic mono- or polycyclic radicals which, besides carbon ring members, can additionally contain one to four nitrogen atoms or one to three nitrogen atoms and one oxygen or one sulfur atom and which are bonded to the skeleton via a nitrogen atom.

The term "partially or fully halogenated" is intended to express that some or all of the hydrogen atoms in those characterized groups can be replaced by identical or different halogen atoms as mentioned above.

Compounds of the formula I which must be emphasized are those where the substituents and the index have the following meanings:

X is NOCH$_3$, CHOCH$_3$ and CHCH$_3$;

Y is oxygen or NR$^a$;

R$^a$ is hydrogen or C$_1$–C$_4$-alkyl;

R is cyano, nitro, trifluoromethyl, halogen, C$_1$–C$_4$-alkyl and C$_1$–C$_4$-alkoxy;

m is 0, 1 or 2, it being possible for the radicals R to be different when m is 2;

R$^1$ is hydrogen or C$_1$–C$_4$-alkyl;

R$^2$ and R$^3$ independently of one another are
hydrogen, cyano, nitro, hydroxyl, amino, halogen, C$_1$–C$_6$-alkyl, C$_1$–C$_6$-alkoxy, C$_1$–C$_6$-alkylthio, C$_1$–C$_6$-alkylamino, di-C$_1$–C$_6$-alkylamino, C$_2$–C$_6$-alkenyl, C$_2$–C$_6$-alkenyloxy, C$_2$–C$_6$-alkenylthio, C$_2$–C$_6$-alkenylamino, N-C$_2$–C$_6$-alkenyl-N-C$_1$–C$_6$-alkylamino, C$_2$–C$_6$-alkynyl, C$_2$–C$_6$-alkynyloxy, C$_2$–C$_6$-alkynylthio, C$_2$–C$_6$-alkynylamino, N-C$_2$–C$_6$-alkynyl-N-C$_1$–C$_6$-alkylamino, it being possible for the hydrocarbon radicals of these groups to be partially or fully halogenated or to have attached to them one to three of the following radicals: cyano, nitro, hydroxyl, mercapto, amino, carboxyl, aminocarbonyl, aminothiocarbonyl, halogen, C$_1$–C$_6$-alkylaminocarbonyl, di-C$_1$–C$_6$-alkylaminocarbonyl, C$_1$–C$_6$-alkylaminothiocarbonyl, di-C$_1$–C$_6$-alkylaminothiocarbonyl, C$_1$–C$_6$-alkylsulfonyl, C$_1$–C$_6$-alkylsulfoxyl, C$_1$–C$_6$-alkoxy, C$_1$–C$_6$-haloalkoxy, C$_1$–C$_6$-alkoxycarbonyl, C$_1$–C$_6$-alkylthio, C$_1$–C$_6$-alkylamino, di-C$_1$–C$_6$-alkylamino, C$_2$–C$_6$-alkenyloxy, C$_3$–C$_6$-cycloalkyl, C$_3$–C$_6$- cycloalkyloxy, heterocyclyl, heterocyclyloxy, aryl, aryloxy, aryl-$C_1$–$C_4$-alkoxy, arylthio, aryl-$C_1$–$C_4$-alkylthio, hetaryl, hetaryloxy, hetaryl-$C_1$–$C_4$-alkoxy, hetarylthio, hetaryl-$C_1$–$C_4$-alkylthio, it being possible for the cyclic radicals, in turn, to be partially or fully halogenated and/or to have attached to them one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyloxy, benzyl, benzyloxy, aryl, aryloxy, arylthio, hetaryl, hetaryloxy, hetarylthio and $C(=NOR^b)$—$A_n$—$R^c$;

$C_3$–$C_6$-cycloalkyl, $C_3$–$C_6$-cycloalkyloxy, $C_3$–$C_6$-cycloalkylthio, $C_3$–$C_6$-cycloalkylamino, N-$C_3$–$C_6$-cycloalkyl-N-$C_1$–$C_6$-alkylamino, $C_3$–$C_6$-cycloalkenyl, $C_3$–$C_6$-cycloalkenyloxy, $C_3$–$C_6$-cycloalkenylthio, $C_3$–$C_6$-cycloalkenylamino, N-$C_3$–$C_6$-cycloalkenyl-N-$C_1$–$C_6$-alkylamino, heterocyclyl, heterocyclyloxy, heterocyclylthio, heterocyclylamino, N-heterocyclyl-N-$C_1$–$C_6$-alkylamino, aryl, aryloxy, arylthio, arylamino, N-aryl-N-$C_1$–$C_6$-alkylamino, hetaryl, hetaryloxy, hetarylthio, hetarylamino, N-hetaryl-N-$C_1$–$C_6$-alkylamino, it being possible for the cyclic radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyloxy, benzyl, benzyloxy, aryl, aryloxy, hetaryl, hetaryloxy, $C(=NOR^b)$—$A_n$—$R^c$ or $NR^f$—CO—D—$R^g$;

A is oxygen, sulfur or nitrogen, the nitrogen having attached to it hydrogen or $C_1$–$C_6$-alkyl;

D is a direct bond, oxygen or $NR^h$;

n is 0 or 1;

$R^b$, $R^c$ independently of one another are hydrogen or $C_1$–$C_6$-alkyl;

$R^f$ is hydrogen, hydroxyl, $C_1$–$C_6$-alkyl, $C_2$–$C_6$-alkenyl, $C_2$–$C_6$-alkynyl, $C_1$–$C_6$-alkoxy-$C_1$–$C_6$-alkyl, $C_1$–$C_6$-alkoxy-$C_1$–$C_6$-alkoxy and $C_1$–$C_6$-alkoxycarbonyl;

$R^g$, $R^h$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl;

$R^4$ is one of the groups mentioned under $R^2$, or a group $CR^d=NOR^e$;

$R^d$ is one of the groups mentioned under $R^2$;

$R^e$ is hydrogen, $C_1$–$C_{10}$-alkyl, $C_2$–$C_6$-alkenyl, $C_2$–$C_{10}$-alkynyl, $C_1$–$C_{10}$-alkylcarbonyl, $C_2$–$C_6$-alkenylcarbonyl, $C_3$–$C_{10}$-alkynylcarbonyl or $C_1$–$C_{10}$-alkylsulfonyl, it being possible for these radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyloxy, $C_3$–$C_6$-cycloalkyl, $C_3$–$C_6$-cycloalkyloxy, heterocyclyl, heterocyclyloxy, benzyl, benzyloxy, aryl, aryloxy, arylthio, hetaryl, hetaryloxy and hetarylthio, it being possible for the 12 last-mentioned groups, in turn, to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio or $C(=NOR^b)$—$A_n$—$R^c$;

$C_3$–$C_6$-cycloalkyl, aryl, arylcarbonyl, arylsulfonyl, hetaryl, hetarylcarbonyl or hetarylsulfonyl, it being possible for these radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkyloxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy, $C(=NOR^b)$—$A_n$—$R^c$ or $NR^f$—CO—D—$R^g$;

and the salts thereof.

With regard to their biological activity, preferred compounds of the formula I are those where m is 0 or 1, in particular 0.

In the event that m is 1, preferred compounds I are those where R is methyl, trifluoromethyl, methoxy, chlorine and fluorine.

Especially preferred compounds I are those where X is $NOCH_3$ (formula I.1).

Furthermore preferred compounds I are those where X is $CHCH_3$ (formula I.2).

Equally preferred compounds I are those where X is $CHOCH_3$ (formula I.3).

Besides, especially preferred compounds I are those where $R^1$ is methyl.

Furthermore, preferred compounds I are those where Y is oxygen (formula Ia).

Equally preferred compounds I are those where Y is $NR^a$, in particular NH (formula Ib).

Also particularly preferred compounds I are those where $R^2$ is hydrogen or $C_1$–$C_4$-alkyl.

Furthermore, especially preferred compounds I are those where $R^2$ is methyl.

Equally especially preferred compounds I are those where $R^2$ is substituted or unsubstituted aryl or hetaryl.

Besides, especially preferred compounds I are those where $R^2$ is substituted or unsubstituted phenyl.

Furthermore, especially preferred compounds I are those where $R^2$ is cyclopropyl.

Compounds I which are also particularly preferred are those where $R^3$ is $C_1$–$C_4$-alkyl, especially methyl.

Furthermore, especially preferred compounds I are those where $R^3$ is hetaryl, especially substituted or unsubstituted pyridinyl, isoxazolyl or pyrazolyl.

Equally, especially preferred compounds I are those where $R^3$ is aryl, in particularly substituted or unsubstituted phenyl.

Besides, especially preferred compounds I are those where $R^3$ is substituted or unsubstituted cycloalkyl, in particular cyclopropyl.

Compounds I which are also particularly preferred are those where $R^4$ is $C_1$–$C_6$-alkyl, especially methyl.

Furthermore, especially preferred compounds I are those where $R^4$ is aryl, especially substituted or unsubstituted phenyl.

Equally, especially preferred compounds I are those where $R^4$ is hetaryl, in particular substituted or unsubstituted pyridinyl, isoxazolyl and pyrazolyl.

Besides, especially preferred compounds I are those where $R^4$ is the group $CR^d$=$NOR^e$.

Besides, preferred compounds I are those where the radical CX—$COYR^1$ is bonded in the 2-position of the pyridyl ring.

Furthermore, preferred compounds I are those where the radical CX—$COYR^1$ is bonded in the 3-position of the pyridyl ring.

Moreover, preferred compounds I are those where the radical CX—$COYR^1$ is bonded in the 4-position of the pyridyl ring.

Besides, compounds I are those where the radical $CH_2O$—$R^2$=N—N=$CR^3R^4$ is bonded in the 2-position of the pyridyl ring.

Furthermore, preferred compounds I are those where the radical $CH_2O$—$R^2$=N—N=$CR^3R^4$ is bonded in the 3-position of the pyridyl ring.

Moreover, preferred compounds I are those where the radical $CH_2O$—$R^2$=N—N=$CR^3R^4$ is bonded in the 4-position of the pyridyl ring.

Compounds I which are also particularly preferred are those where $R^d$ is $C_1$–$C_4$-alkyl, especially methyl.

Moreover, preferred compounds I are also those where $R^d$ is hetaryl, especially substituted or unsubstituted pyridinyl, isoxazolyl and pyrazolyl.

Besides, preferred compounds I are also those where $R^d$ is aryl, especially substituted or unsubstituted phenyl.

Equally, preferred compounds I are also those where $R^d$ is substituted or unsubstituted cycloalkyl, especially cyclopropyl.

In particular, preferred compounds I are also those where $R^e$ is $C_1$–$C_4$-alkyl, especially methyl.

Moreover, preferred compounds I are also those where $R^e$ is substituted or unsubstituted alkenyl, especially allyl and trans-chloroallyl.

Equally, preferred compounds I are also those where $R^e$ is substituted or unsubstituted alkynyl, especially propargyl, bromo- and iodopropargyl.

Furthermore, preferred compounds I are also those where $R^e$ is alkoxyalkyl, especially $C_1$–$C_2$-alkoxy-$C_1$–$C_2$-alkyl.

Besides, preferred compounds I are also those where $R^e$ is arylalkyl, especially phenyl-$C_1$–$C_2$-alkyl which is unsubstituted or substituted in the phenyl moiety.

Equally, preferred compounds I are also those where $R^e$ is substituted or unsubstituted hetaryl or hetarylalkyl.

Particularly preferred regarding their use are the compounds I compiled in the Tables which follow. Moreover, the groups mentioned in the Tables for a given substituent are, on their own (independently of the combination in which they are mentioned), an especially preferred embodiment of the substituent in question.

Table 1

Compounds of the general formula IA.1 where $R^2$ is methyl, $R^3$ is methyl and $R^4$ is $R^x$-substituted phenyl, $R^x$ for a given compound in each case corresponding to one line of Table A

IA.1

[Structure: pyridine ring with $CH_2OCR^2$=NN=$CR^3R^4$ substituent and =$NOCH_3$ / $CO_2CH_3$ substituent]

Table 2

Compounds of the general formula IA.2 where $R^2$ is methyl, $R^3$ is methyl and $R^4$ is $R^x$-substituted phenyl, $R^x$ for a given compound in each case corresponding to one line of Table A

IA.2

[Structure: pyridine ring with $CH_2OCR^2$=NN=$CR^3R^4$ substituent and =$CHCH_3$ / $CO_2CH_3$ substituent]

Table 3

Compounds of the general formula IA.3 where $R^2$ is methyl, $R^3$ is methyl and $R^4$ is $R^x$-substituted phenyl, $R^x$ for a given compound in each case corresponding to one line of Table A

IA.3

[Structure: pyridine ring with $CH_2OCR^2$=NN=$CR^3R^4$ substituent and =$CHOCH_3$ / $CO_2CH_3$ substituent]

Table 4

Compounds of the general formula IB.1 where $R^2$ is methyl, $R^3$ is methyl and $R^4$ is $R^x$-substituted phenyl, $R^x$ for a given compound in each case corresponding to one line of Table A

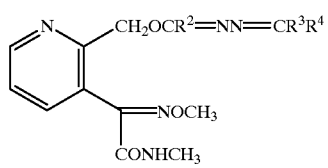

IB.1

Table 5

Compounds of the formula IA.1 where combination of the radicals $R^2$, $R^3$ and $R^4$ for a given compound corresponds in each case to one line of Table B Table 6

Compounds of the formula IA.2 where combination of the radicals $R^2$, $R^3$ and $R^4$ for a given compound corresponds in each case to one line of Table B Table 7

Compounds of the formula IA.3 where combination of the radicals $R^2$, $R^3$ and $R^4$ for a given compound corresponds in each case to one line of Table B Table 8

Compounds of the formula IB.1 where combination of the radicals $R^2$, $R^3$ and $R^4$ for a given compound corresponds in each case to one line of Table B Table 9

Compounds of the formula IA.1.1 where $R^2$, $R^d$ and $R^e$ are in each case methyl and $R^3$ is $R^x$-substituted phenyl, $R^x$ for a given compound in each case corresponding to one line of Table A

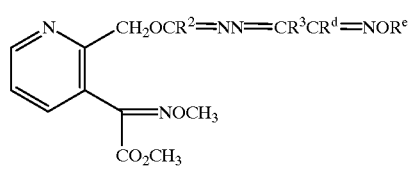

IA.1.1

Table 10

Compounds of the formula IA.2.1 where $R^2$, $R^d$ and $R^e$ are in each case methyl and $R^3$ is $R^x$-substituted phenyl, $R^x$ for a given compound in each case corresponding to one line of Table A

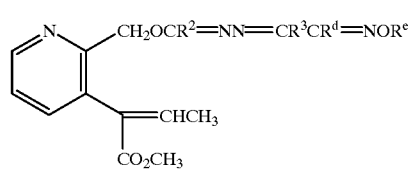

IA.2.1

Table 11

Compounds of the formula IA.3.1 where $R^2$, $R^d$ and $R^e$ are in each case methyl and $R^3$ is $R^x$-substituted phenyl, $R^x$ for a given compound in each case corresponding to one line of Table A

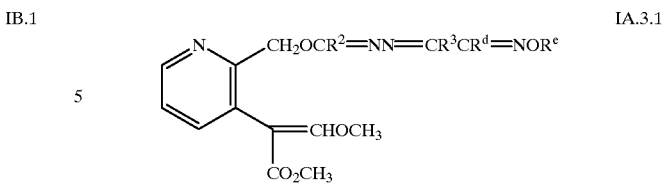

IA.3.1

Table 12

Compounds of the formula IB.1.1 where $R^2$, $R^d$ and $R^e$ are in each case methyl and $R^3$ is $R^x$-substituted phenyl, $R^x$ for a given compound in each case corresponding to one line of Table A

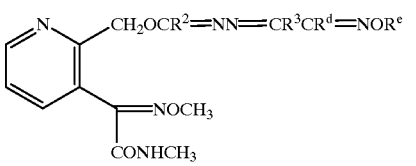

IB.1.1

Table 13

Compounds of the formula IA.1.1 where $R^2$ is ethyl, $R^d$ and $R^e$ are in each case methyl and $R^3$ is $R^x$-substituted phenyl, $R^x$ for a given compound in each case corresponding to one line of Table A Table 14

Compounds of the formula IA.2.1 where $R^2$ is ethyl, $R^d$ and $R^e$ are in each case methyl and $R^3$ is $R^x$-substituted phenyl, $R^x$ for a given compound in each case corresponding to one line of Table A Table 15

Compounds of the formula IA.3.1 where $R^2$ is ethyl, $R^d$ and $R^e$ are in each case methyl and $R^3$ is $R^x$-substituted phenyl, $R^x$ for a given compound in each case corresponding to one line of Table A Table 16

Compounds of the formula IB.1.1 where $R^2$ is ethyl, $R^d$ and $R^e$ are in each case methyl and $R^3$ is $R^x$-substituted phenyl, $R^x$ for a given compound in each case corresponding to one line of Table A Table 17

Compounds of the formula IA.1.1 where $R^2$ is cyclopropyl, $R^d$ and $R^e$ are in each case methyl and $R^3$ is $R^x$-substituted phenyl, $R^x$ for a given compound in each case corresponding to one line of Table A Table 18

Compounds of the formula IA.2.1 where $R^2$ is cyclopropyl, $R^d$ and $R^e$ are in each case methyl and $R^3$ is $R^x$-substituted phenyl, $R^x$ for a given compound in each case corresponding to one line of Table A Table 19

Compounds of the formula IA.3.1 where $R^2$ is cyclopropyl, $R^d$ and $R^e$ are in each case methyl and $R^3$ is $R^x$-substituted phenyl, $R^x$ for a given compound in each case corresponding to one line of Table A Table 20

Compounds of the formula IB.1.1 where $R^2$ is cyclopropyl, $R^d$ and $R^e$ are in each case methyl and $R^3$ is $R^x$-substituted phenyl, $R^x$ for a given compound in each case corresponding to one line of Table A Table 21

Compounds of the formula IA.1.1 where $R^2$ is methyl, $R^3$ and $R^e$ are in each case methyl and $R^d$ is $R^x$-substituted phenyl, $R^x$ for a given compound in each case corresponding to one line of Table A Table 22

Compounds of the formula IA.2.1 where $R^2$ is methyl, $R^3$ and $R^e$ are in each case methyl and $R^d$ is $R^x$-substituted phenyl, $R^x$ for a given compound in each case corresponding to one line of Table A Table 23

Compounds of the formula IA.3.1 where $R^2$ is methyl, $R^3$ and $R^e$ are in each case methyl and $R^d$ is $R^x$-substituted phenyl, $R^x$ for a given compound in each case corresponding to one line of Table A Table 24

Compounds of the formula IB.1.1 where $R^2$ is methyl, $R^3$ and $R^e$ are in each case methyl and $R^d$ is $R^x$-substituted phenyl, $R^x$ for a given compound in each case corresponding to one line of Table A Table 25

Compounds of the formula IA.1.1 where $R^3$ is ethyl, $R^2$ and $R^e$ are in each case methyl and $R^d$ is $R^x$-substituted phenyl, $R^x$ for a given compound in each case corresponding to one line of Table A Table 26

Compounds of the formula IA.2.1 where $R^3$ is ethyl, $R^2$ and $R^e$ are in each case methyl and $R^d$ is $R^x$-substituted phenyl, $R^x$ for a given compound in each case corresponding to one line of Table A Table 27

Compounds of the formula IA.3.1 where $R^3$ is ethyl, $R^2$ and $R^e$ are in each case methyl and $R^d$ is $R^x$-substituted phenyl, $R^x$ for a given compound in each case corresponding to one line of Table A Table 28

Compounds of the formula IB.1.1 where $R^3$ is ethyl, $R^2$ and $R^e$ are in each case methyl and $R^d$ is $R^x$-substituted phenyl, $R^x$ for a given compound in each case corresponding to one line of Table A Table 29

Compounds of the formula IA.1.1 where $R^3$ is isopropyl, $R^2$ and $R^e$ are in each case methyl and $R^d$ is $R^x$-substituted phenyl, $R^x$ for a given compound in each case corresponding to one line of Table A Table 30

Compounds of the formula IA.2.1 where $R^3$ is isopropyl, $R^2$ and $R^e$ are in each case methyl and $R^d$ is $R^x$-substituted phenyl, $R^x$ for a given compound in each case corresponding to one line of Table A Table 31

Compounds of the formula IA.3.1 where $R^3$ is isopropyl, $R^2$ and $R^e$ are in each case methyl and $R^d$ is $R^x$-substituted phenyl, $R^x$ for a given compound in each case corresponding to one line of Table A Table 32

Compounds of the formula IB.1.1 where $R^3$ is isopropyl, $R^2$ and $R^e$ are in each case methyl and $R^d$ is $R^x$-substituted phenyl, $R^x$ for a given compound in each case corresponding to one line of Table A Table 33

Compounds of the formula IA.1.1 where $R^e$ is ethyl, $R^2$ and $R^3$ are in each case methyl and $R^d$ is $R^x$-substituted phenyl, $R^x$ for a given compound in each case corresponding to one line of Table A Table 34

Compounds of the formula IA.2.1 where $R^e$ is ethyl, $R^2$ and $R^3$ are in each case methyl and $R^d$ is $R^x$-substituted phenyl, $R^x$ for a given compound in each case corresponding to one line of Table A Table 35

Compounds of the formula IA.3.1 where $R^e$ is ethyl, $R^2$ and $R^3$ are in each case methyl and $R^d$ is $R^x$-substituted phenyl, $R^x$ for a given compound in each case corresponding to one line of Table A Table 36

Compounds of the formula IB.1.1 where $R^e$ is ethyl, $R^2$ and $R^3$ are in each case methyl and $R^d$ is $R^x$-substituted phenyl, $R^x$ for a given compound in each case corresponding to one line of Table A Table 37

Compounds of the formula IA.1.1 where $R^e$ is n-propyl, $R^2$ and $R^3$ are in each case methyl and $R^d$ is $R^x$-substituted phenyl, $R^x$ for a given compound in each case corresponding to one line of Table A Table 38

Compounds of the formula IA.2.1 where $R^e$ is n-propyl, $R^2$ and $R^3$ are in each case methyl and $R^d$ is $R^x$-substituted phenyl, $R^x$ for a given compound in each case corresponding to one line of Table A Table 39

Compounds of the formula IA.3.1 where $R^e$ is n-propyl, $R^2$ and $R^3$ are in each case methyl and $R^d$ is $R^x$-substituted phenyl, $R^x$ for a given compound in each case corresponding to one line of Table A Table 40

Compounds of the formula IB.1.1 where $R^e$ is n-propyl, $R^2$ and $R^3$ are in each case methyl and $R^d$ is $R^x$-substituted phenyl, $R^x$ for a given compound in each case corresponding to one line of Table A Table 41

Compounds of the formula IA.1.1 where $R^e$ is isopropyl, $R^2$ and $R^3$ are in each case methyl and $R^d$ is $R^x$-substituted phenyl, $R^x$ for a given compound in each case corresponding to one line of Table A Table 42

Compounds of the formula IA.2.1 where $R^e$ is isopropyl, $R^2$ and $R^3$ are in each case methyl and $R^d$ is $R^x$-substituted phenyl, $R^x$ for a given compound in each case corresponding to one line of Table A Table 43

Compounds of the formula IA.3.1 where $R^e$ is isopropyl, $R^2$ and $R^3$ are in each case methyl and $R^d$ is $R^x$-substituted phenyl, $R^x$ for a given compound in each case corresponding to one line of Table A Table 44

Compounds of the formula IB.1.1 where $R^e$ is isopropyl, $R^2$ and $R^3$ are in each case methyl and $R^d$ is $R^x$-substituted phenyl, $R^x$ for a given compound in each case corresponding to one line of Table A Table 45

Compounds of the formula IA.1.1 where $R^e$ is tert-butyl, $R^2$ and $R^3$ are in each case methyl and $R^d$ is $R^x$-substituted phenyl, $R^x$ for a given compound in each case corresponding to one line of Table A Table 46

Compounds of the formula IA.2.1 where $R^e$ is tert-butyl, $R^2$ and $R^3$ are in each case methyl and $R^d$ is $R^x$-substituted phenyl, $R^x$ for a given compound in each case corresponding to one line of Table A Table 47

Compounds of the formula IA.3.1 where $R^e$ is tert-butyl, $R^2$ and $R^3$ are in each case methyl and $R^d$ is $R^x$-substituted phenyl, $R^x$ for a given compound in each case corresponding to one line of Table A Table 48

Compounds of the formula IB.1.1 where $R^e$ is tert-butyl, $R^2$ and $R^3$ are in each case methyl and $R^d$ is $R^x$-substituted phenyl, $R^x$ for a given compound in each case corresponding to one line of Table A Table 49
Compounds of the formula IA.1.1 where $R^e$ is benzyl, $R^2$ and $R^3$ are in each case methyl and $R^d$ is $R^x$-substituted phenyl, $R^x$ for a given compound in each case corresponding to one line of Table A Table 50
Compounds of the formula IA.2.1 where $R^e$ is benzyl, $R^2$ and $R^3$ are in each case methyl and $R^d$ is $R^x$-substituted phenyl, $R^x$ for a given compound in each case corresponding to one line of Table A Table 51
Compounds of the formula IA.3.1 where $R^e$ is benzyl, $R^2$ and $R^3$ are in each case methyl and $R^d$ is $R^x$-substituted phenyl, $R^x$ for a given compound in each case corresponding to one line of Table A Table 52
Compounds of the formula IB.1.1 where $R^e$ is benzyl, $R^2$ and $R^3$ are in each case methyl and $R^d$ is $R^x$-substituted phenyl, $R^x$ for a given compound in each case corresponding to one line of Table A Table 53
Compounds of the formula IA.1.1 where $R^e$ is propargyl, $R^2$ and $R^3$ are in each case methyl and $R^d$ is $R^x$-substituted phenyl, $R^x$ for a given compound in each case corresponding to one line of Table A Table 54
Compounds of the formula IA.2.1 where $R^e$ is propargyl, $R^2$ and $R^3$ are in each case methyl and $R^d$ is $R^x$-substituted phenyl, $R^x$ for a given compound in each case corresponding to one line of Table A Table 55
Compounds of the formula IA.3.1 where $R^e$ is propargyl, $R^2$ and $R^3$ are in each case methyl and $R^d$ is $R^x$-substituted phenyl, $R^x$ for a given compound in each case corresponding to one line of Table A Table 56
Compounds of the formula IB.1.1 where $R^e$ is propargyl, $R^2$ and $R^3$ are in each case methyl and $R^d$ is $R^x$-substituted phenyl, $R^x$ for a given compound in each case corresponding to one line of Table A Table 57
Compounds of the formula IA.1.1 where $R^e$ is bromopropargyl, $R^2$ and $R^3$ are in each case methyl and $R^d$ is $R^x$-substituted phenyl, $R^x$ for a given compound in each case corresponding to one line of Table A Table 58
Compounds of the formula IA.2.1 where $R^e$ is bromopropargyl, $R^2$ and $R^3$ are in each case methyl and $R^d$ is $R^x$-substituted phenyl, $R^x$ for a given compound in each case corresponding to one line of Table A Table 59
Compounds of the formula IA.3.1 where $R^e$ is bromopropargyl, $R^2$ and $R^3$ are in each case methyl and $R^d$ is $R^x$-substituted phenyl, $R^x$ for a given compound in each case corresponding to one line of Table A Table 60
Compounds of the formula IB.1.1 where $R^e$ is bromopropargyl, $R^2$ and $R^3$ are in each case methyl and $R^d$ is $R^x$-substituted phenyl, $R^x$ for a given compound in each case corresponding to one line of Table A Table 61
Compounds of the formula IA.1.1 where $R^e$ is iodopropargyl, $R^2$ and $R^3$ are in each case methyl and $R^d$ is $R^x$-substituted phenyl $R^x$ for a given compound in each case corresponding to one line of Table A Table 62
Compounds of the formula IA.2.1 where $R^e$ is iodopropargyl, $R^2$ and $R^3$ are in each case methyl and $R^d$ is $R^x$-substituted phenyl, $R^x$ for a given compound in each case corresponding to one line of Table A Table 63
Compounds of the formula IA.3.1 where $R^e$ is iodopropargyl, $R^2$ and $R^3$ are in each case methyl and $R^d$ is $R^x$-substituted phenyl, $R^x$ for a given compound in each case corresponding to one line of Table A Table 64
Compounds of the formula IB.1.1 where $R^e$ is iodopropargyl, $R^2$ and $R^3$ are in each case methyl and $R^d$ is $R^x$-substituted phenyl, $R^x$ for a given compound in each case corresponding to one line of Table A Table 65
Compounds of the formula IA.1.1 where $R^e$ is allyl, $R^2$ and $R^3$ are in each case methyl and $R^d$ is $R^x$-substituted phenyl, $R^x$ for a given compound in each case corresponding to one line of Table A Table 66
Compounds of the formula IA.2.1 where $R^e$ is allyl, $R^2$ and $R^3$ are in each case methyl and $R^d$ is $R^x$-substituted phenyl, $R^x$ for a given compound in each case corresponding to one line of Table A Table 67
Compounds of the formula IA.3.1 where $R^e$ is allyl, $R^2$ and $R^3$ are in each case methyl and $R^d$ is $R^x$-substituted phenyl, $R^x$ for a given compound in each case corresponding to one line of Table A Table 68
Compounds of the formula IB.1.1 where $R^e$ is allyl, $R^2$ and $R^3$ are in each case methyl and $R^d$ is $R^x$-substituted phenyl, $R^x$ for a given compound in each case corresponding to one line of Table A Table 69
Compounds of the formula IA.1.1 where $R^e$ is trans-chloroallyl, $R^2$ and $R^3$ are in each case methyl and $R^d$ is $R^x$-substituted phenyl, $R^x$ for a given compound in each case corresponding to one line of Table A Table 70
Compounds of the formula IA.2.1 where $R^e$ is trans-chloroallyl, $R^2$ and $R^3$ are in each case methyl and $R^d$ is $R^x$-substituted phenyl, $R^x$ for a given compound in each case corresponding to one line of Table A Table 71
Compounds of the formula IA.3.1 where $R^e$ is trans-chloroallyl, $R^2$ and $R^3$ are in each case methyl and $R^d$ is $R^x$-substituted phenyl, $R^x$ for a given compound in each case corresponding to one line of Table A Table 72
Compounds of the formula IB.1.1 where $R^e$ is trans-chloroallyl, $R^2$ and $R^3$ are in each case methyl and $R^d$ is $R^x$-substituted phenyl, $R^x$ for a given compound in each case corresponding to one line of Table A Table 73
Compounds of the formula IA.1.1 where $R^e$ is methoxyethyl, $R^2$ and $R^3$ are in each case methyl and $R^d$ is $R^x$-substituted phenyl, $R^x$ for a given compound in each case corresponding to one line of Table A Table 74
Compounds of the formula IA.2.1 where $R^e$ is methoxyethyl, $R^2$ and $R^3$ are in each case methyl and $R^d$ is $R^x$-substituted phenyl, $R^x$ for a given compound in each case corresponding to one line of Table A Table 75
Compounds of the formula IA.3.1 where $R^e$ is methoxyethyl, $R^2$ and $R^3$ are in each case methyl and $R^d$ is $R^x$-substituted phenyl, $R^x$ for a given compound in each case corresponding to one line of Table A Table 76

Compounds of the formula IB.1.1 where $R^e$ is methoxyethyl, $R^2$ and $R^3$ are in each case methyl and $R^d$ is $R^x$-substituted phenyl, $R^x$ for a given compound in each case corresponding to one line of Table A Table 77

Compounds of the formula IA.1.1, where $R^2$, $R^3$, $R^d$ and $R^e$ have the meanings mentioned in Table C Table 78

Compounds of the formula IA.2.1, where $R^2$, $R^3$, $R^d$ and $R^e$ have the meanings mentioned in Table C Table 79

Compounds of the formula IA.3.1, where $R^2$, $R^3$, $R^d$ and $R^e$ have the meanings mentioned in Table C Table 80

Compounds of the formula IB.1.1, where $R^2$, $R^3$, $R^d$ and $R^e$ have the meanings mentioned in Table C

TABLE A

| No. | $R^x$ |
|---|---|
| 01 | H |
| 02 | 2-F |
| 03 | 3-F |
| 04 | 4-F |
| 05 | 2,4-$F_2$ |
| 06 | 2,3-$F_2$ |
| 07 | 2,4,6-$F_3$ |
| 08 | 2,3,4,5,6-$F_5$ |
| 09 | 2-Cl |
| 10 | 3-Cl |
| 11 | 4-Cl |
| 12 | 2,3-$Cl_2$ |
| 13 | 2,4-$Cl_2$ |
| 14 | 2,5-$Cl_2$ |
| 15 | 2,6-$Cl_2$ |
| 16 | 3,4-$Cl_2$ |
| 17 | 3,5-$Cl_2$ |
| 18 | 2,3,4-$Cl_3$ |
| 19 | 2,3,5-$Cl_3$ |
| 20 | 2,3,6-$Cl_3$ |
| 21 | 2,4,5-$Cl_3$ |
| 22 | 2,4,6-$Cl_3$ |
| 23 | 3,4,5-$Cl_3$ |
| 24 | 2,3,4,6-$Cl_4$ |
| 25 | 2,3,5,6-$Cl_4$ |
| 26 | 2,3,4,5,6-$Cl_5$ |
| 27 | 2-Br |
| 28 | 3-Br |
| 29 | 4-Br |
| 30 | 2,4-$Br_2$ |
| 31 | 2,5-$Br_2$ |
| 32 | 2,6-$Br_2$ |
| 33 | 2,4,6-$Br_3$ |
| 34 | 2,3,4,5,6-$Br_5$ |
| 35 | 2-I |
| 36 | 3-I |
| 37 | 4-I |
| 38 | 2,4-$I_2$ |
| 39 | 2-Cl, 3-F |
| 40 | 2-Cl, 4-F |
| 41 | 2-Cl, 5-F |
| 42 | 2-Cl, 6-F |
| 43 | 2-Cl, 3-Br |
| 44 | 2-Cl, 4-Br |
| 45 | 2-Cl, 5-Br |
| 46 | 2-Cl, 6-Br |
| 47 | 2-Br, 3-Cl |
| 48 | 2-Br, 4-Cl |
| 49 | 2-Br, 5-Cl |
| 50 | 2-Br, 6-Cl |
| 51 | 2-Br, 3-F |

TABLE A-continued

| No. | $R^x$ |
|---|---|
| 52 | 2-Br, 4-F |
| 53 | 2-Br, 5-F |
| 54 | 2-Br, 6-F |
| 55 | 2-F, 3-Cl |
| 56 | 2-F, 4-Cl |
| 57 | 2-F, 5-Cl |
| 58 | 4-F, 3-Cl |
| 59 | 5-F, 3-Cl |
| 60 | 4-Br, 3-Cl |
| 61 | 5-Br, 3-Cl |
| 62 | 3-F, 4-Cl |
| 63 | 3-F, 4-Br |
| 64 | 3-Br, 4-Cl |
| 65 | 4-F, 3-Br |
| 66 | 2,6-$Cl_2$, 4-Br |
| 67 | 2-$CH_3$ |
| 68 | 3-$CH_3$ |
| 69 | 4-$CH_3$ |
| 70 | 2,3-$(CH_3)_2$ |
| 71 | 2,4-$(CH_3)_2$ |
| 72 | 2,5-$(CH_3)_2$ |
| 73 | 2,6-$(CH_3)_2$ |
| 74 | 3,4-$(CH_3)_2$ |
| 75 | 3,5-$(CH_3)_2$ |
| 76 | 2,3,4-$(CH_3)_3$ |
| 77 | 2,3,5-$(CH_3)_3$ |
| 78 | 2,3,6-$(CH_3)_3$ |
| 79 | 2,4,5-$(CH_3)_3$ |
| 80 | 2,4,6-$(CH_3)_3$ |
| 81 | 3,4,5-$(CH_3)_3$ |
| 82 | 2,3,4,6-$(CH_3)_4$ |
| 83 | 2,3,5,6-$(CH_3)_4$ |
| 84 | 2,3,4,5,6-$(CH_3)5$ |
| 85 | 2-$C_2H_5$ |
| 86 | 3-$C_2H_5$ |
| 87 | 4-$C_2H_5$ |
| 88 | 2,4-$(C_2H_5)_2$ |
| 89 | 2,6-$(C_2H_5)_2$ |
| 90 | 3,5-$(C_2H_5)_2$ |
| 91 | 2,4,6-$(C_2H_5)_3$ |
| 92 | 2-n-$C_3H_7$ |
| 93 | 3-n-$C_3H_7$ |
| 94 | 4-n-$C_3H_7$ |
| 95 | 2-i-$C_3H_7$ |
| 96 | 3-i-$C_3H_7$ |
| 97 | 4-i-$C_3H_7$ |
| 98 | 2,4-$(i-C_3H_7)_2$ |
| 99 | 2,6-$(i-C_3H_7)_2$ |
| 100 | 3,5-$(i-C_3H_7)_2$ |
| 101 | 2-s-$C_4H_9$ |
| 102 | 3-s-$C_4H_9$ |
| 103 | 4-s-$C_4H_9$ |
| 104 | 2-t-$C_4H_9$ |
| 105 | 3-t-$C_4H_9$ |
| 106 | 4-t-$C_4H_9$ |
| 107 | 4-n-$C_9H_{19}$ |
| 108 | 2-$CH_3$, 4-t-$C_4H_9$ |
| 109 | 2-$CH_3$, 6-t-$C_4H_9$ |
| 110 | 2-$CH_3$, 4-i-$C_3H_7$ |
| 111 | 2-$CH_3$, 5-i-$C_3H_7$ |
| 112 | 3-$CH_3$, 4-i-$C_3H_7$ |
| 113 | 2-c-$C_6H_{11}$ |
| 114 | 3-c-$C_6H_{11}$ |
| 115 | 4-c-$C_6H_{11}$ |
| 116 | 2-Cl, 4-$C_6H_5$ |
| 117 | 2-Br, 4-$C_6H_5$ |
| 118 | 2-$OCH_3$ |
| 119 | 3-$OCH_3$ |
| 120 | 4-$OCH_3$ |
| 121 | 2-$OC_2H_5$ |
| 122 | 3-$OC_2H_5$ |
| 123 | 4-$OC_2H_5$ |
| 124 | 2-O-n-$C_3H_7$ |
| 125 | 3-O-n-$C_3H_7$ |
| 126 | 4-O-n-$C_3H_7$ |
| 127 | 2-O-i-$C_3H_7$ |
| 128 | 3-O-i-$C_3H_7$ |

TABLE A-continued

| No. | $R^x$ |
|---|---|
| 129 | 4-O-i-$C_3H_7$ |
| 130 | 2-O-n-$C_6H_{13}$ |
| 131 | 3-O-n-$C_6H_{13}$ |
| 132 | 4-O-n-$C_6H_{13}$ |
| 133 | 2-$OCH_2C_6H_5$ |
| 134 | 3-$OCH_2C_6H_5$ |
| 135 | 4-$OCH_2C_6H_5$ |
| 136 | 2-O$(CH_2)_2C_6H_5$ |
| 137 | 4-O$(CH_2)_2C_6H_5$ |
| 138 | 2,3-$(OCH_3)_2$ |
| 139 | 2,4-$(OCH_3)_2$ |
| 140 | 2,5-$(OCH_3)_2$ |
| 141 | 2,6-$(OCH_3)_2$ |
| 142 | 3,4-$(OCH_3)_2$ |
| 143 | 3,5-$(OCH_3)_2$ |
| 144 | 2-O-t-$C_4H_9$ |
| 145 | 3-O-t-$C_4H_9$ |
| 146 | 4-O-t-$C_4H_9$ |
| 147 | 3-(3'-Cl-$C_6H_4$) |
| 148 | 4-(4'-Cl-$C_6H_4$) |
| 149 | 2-$OC_6H_5$ |
| 150 | 3-$OC_6H_5$ |
| 151 | 4-$OC_6H_5$ |
| 152 | 2-O-(2'-F—$C_6H_4$) |
| 153 | 3-O-(3'-Cl—$C_6H_4$) |
| 154 | 4-O-(4'-$CH_3$—$C_6H_4$) |
| 155 | 2,3,6-$(CH_3)_3$, 4-F |
| 156 | 2,3,6-$(CH_3)_3$, 4-Cl |
| 157 | 2,3,6-$(CH_3)_3$, 4-Br |
| 158 | 2,4-$(CH_3)_2$, 6-F |
| 159 | 2,4-$(CH_3)_2$, 6-Cl |
| 160 | 2,4-$(CH_3)_2$, 6-Br |
| 161 | 2-i-$C_3H_7$, 4-Cl, 5-$CH_3$ |
| 162 | 2-Cl, 4-$NO_2$ |
| 163 | 4-Cl, 2-$NO_2$ |
| 164 | 2-$OCH_3$, 4-$NO_2$ |
| 165 | 2,4-$Cl_2$, 5-$NO_2$ |
| 166 | 2,4-$Cl_2$, 6-$NO_2$ |
| 167 | 2,6-$Cl_2$, 4-$NO_2$ |
| 168 | 2,6-$Br_2$, 4-$NO_2$ |
| 169 | 2,6-$I_2$, 4-$NO_2$ |
| 170 | 2-$CH_3$, 4-Cl, 5-i-$C_3H_7$ |
| 171 | 2-$CO_2CH_3$ |
| 172 | 3-$CO_2CH_3$ |
| 173 | 4-$CO_2CH_3$ |
| 174 | 2-$CH_2OCH_3$ |
| 175 | 3-$CH_2OCH_3$ |
| 176 | 4-$CH_2OCH_3$ |
| 177 | 2-$CH_3$, 4-CO-i-$C_3H_7$ |
| 178 | 2-$CH_3$, 4-C($CH_3$)=$NOCH_3$ |
| 179 | 2-$CH_3$, 4-C($CH_3$)=$NOC_2H_5$ |
| 180 | 2-$CH_3$, 4-C($CH_3$)=NO-n-$C_3H_7$ |
| 181 | 2-$CH_3$, 4-C($CH_3$)=NO-i-$C_3H_7$ |
| 182 | 2,5-$(CH_3)_2$, 4-C($CH_3$)=$NOCH_3$ |
| 183 | 2,5-$(CH_3)_2$, 4-C($CH_3$)=$NOC_2H_5$ |
| 184 | 2,5-$(CH_3)_2$, 4-C($CH_3$)=NO-n-$C_3H_7$ |
| 185 | 2,5-$(CH_3)_2$, 4-C($CH_3$)=NO-i-$C_3H_7$ |
| 186 | 2-$C_6H_5$ |
| 187 | 3-$C_6H_5$ |
| 188 | 4-$C_6H_5$ |
| 189 | 2-(2'-F—$C_6H_4$) |
| 190 | 2-$CH_3$, 5-Br |
| 191 | 2-$CH_3$, 6-Br |
| 192 | 3-$CH_3$, 2-Cl |
| 193 | 4-$CH_3$, 2-Cl |
| 194 | 5-$CH_3$, 2-Cl |
| 195 | 3-$CH_3$, 2-F |
| 196 | 4-$CH_3$, 2-F |
| 197 | 5-$CH_3$, 2-F |
| 198 | 3-$CH_3$, 2-Br |
| 199 | 4-$CH_3$, 2-Br |
| 200 | 5-$CH_3$, 2-Br |
| 201 | 3-$CH_3$, 4-Cl |
| 202 | 5-$CH_3$, 5-Cl |
| 203 | 3-$CH_3$, 4-F |
| 204 | 3-$CH_3$, 5-F |
| 205 | 3-$CH_3$, 4-Br |
| 206 | 3-$CH_3$, 5-Br |
| 207 | 4-$CH_3$, 3-F |
| 208 | 4-$CH_3$, 3-Cl |
| 209 | 4-$CH_3$, 3-Br |
| 210 | 4,5-$(CH_3)_2$, 2-Cl |
| 211 | 4,5-$(CH_3)_2$, 2-Br |
| 212 | 3,5-$(CH_3)_2$, 2-Cl |
| 213 | 3,5-$(CH_3)_2$, 2-Br |
| 214 | 2,6-$Cl_2$, 4-$CH_3$ |
| 215 | 2,6-$F_2$, 4-$CH_3$ |
| 216 | 2,6-$Br_2$, 4-$CH_3$ |
| 217 | 2,4-$Br_2$, 6-$CH_3$ |
| 218 | 2,4-$F_2$, 6-$CH_3$ |
| 219 | 2,4-$Cl_2$, 6-$CH_3$ |
| 220 | 2,6-$(CH_3)_2$, 4-F |
| 221 | 2,6-$(CH_3)_2$, 4-Cl |
| 222 | 2,6-$(CH_3)_2$, 4-Br |
| 223 | 3,5-$(CH_3)_2$, 4-F |
| 224 | 3,5-$(CH_3)_2$, 4-Cl |
| 225 | 3,5-$(CH_3)_2$, 4-Br |
| 226 | 2-$CF_3$ |
| 227 | 3-$CF_3$ |
| 228 | 4-$CF_3$ |
| 229 | 2-$OCF_3$ |
| 230 | 3-$OCF_3$ |
| 231 | 4-$OCF_3$ |
| 232 | 3-$OCH_2CHF_2$ |
| 233 | 2-$NO_2$ |
| 234 | 3-$NO_2$ |
| 235 | 4-$NO_2$ |
| 236 | 2-CN |
| 237 | 3-CN |
| 238 | 4-CN |
| 239 | 2-$CH_3$, 3-Cl |
| 240 | 2-$CH_3$, 4-Cl |
| 241 | 2-$CH_3$, 5-Cl |
| 242 | 2-$CH_3$, 6-Cl |
| 243 | 2-$CH_3$, 3-F |
| 244 | 2-$CH_3$, 4-F |
| 245 | 2-$CH_3$, 5-F |
| 246 | 2-$CH_3$, 6-F |
| 247 | 2-$CH_3$, 3-Br |
| 248 | 2-$CH_3$, 4-Br |
| 249 | 2-$CH_3$, 5-Br |
| 250 | 2-$CH_3$, 6-Br |
| 251 | 2,5-$F_2$ |
| 252 | 2,6-$F_2$ |
| 253 | 3,4-$F_2$ |
| 254 | 3,5-$F_2$ | n = neo; i = iso; s = secondary; t = tertiary; c = cyclo

TABLE B

| No. | $R^2$ | $R^3$ | $R^4$ |
|---|---|---|---|
| 1 | H | $CH_3$ | phenyl |
| 2 | $C_2H_5$ | $CH_3$ | phenyl |
| 3 | n-$C_3H_7$ | $CH_3$ | phenyl |
| 4 | i-$C_3H_7$ | $CH_3$ | phenyl |
| 5 | cyclopropyl | $CH_3$ | phenyl |
| 6 | pyrid-2-yl | $CH_3$ | phenyl |
| 7 | pyrid-3-yl | $CH_3$ | phenyl |
| 8 | pyrid-4-yl | $CH_3$ | phenyl |
| 9 | 5-$CH_3$-isoxazol-3-yl | $CH_3$ | phenyl |
| 10 | phenyl | $CH_3$ | phenyl |
| 11 | $CH_3$ | H | phenyl |
| 12 | $CH_3$ | $C_2H_5$ | phenyl |
| 13 | $CH_3$ | n-$C_3H_7$ | phenyl |
| 14 | $CH_3$ | i-$C_3H_7$ | phenyl |
| 15 | $CH_3$ | cyclopropyl | phenyl |
| 16 | $CH_3$ | pyrid-2-yl | phenyl |
| 17 | $CH_3$ | pyrid-3-yl | phenyl |
| 18 | $CH_3$ | pyrid-4-yl | phenyl |
| 19 | $CH_3$ | 3-$CH_3$-isoxazol-5-yl | phenyl |

TABLE B-continued

| No. | R² | R³ | R⁴ |
|---|---|---|---|
| 20 | CH³ | phenyl | phenyl |
| 21 | H | CH₃ | CH₃ |
| 22 | CH₃ | CH₃ | CH₃ |
| 23 | C₂H₅ | CH₃ | CH₃ |
| 24 | n-C₃H₇ | CH₃ | CH₃ |
| 25 | i-C₃H₇ | CH₃ | CH₃ |
| 26 | cyclopropyl | CH₃ | CH₃ |
| 27 | pyrid-2-yl | CH₃ | CH₃ |
| 28 | pyrid-3-yl | CH₃ | CH₃ |
| 29 | pyrid-4-yl | CH₃ | CH₃ |
| 30 | 5-CH₃-isoxazol-3-yl | CH₃ | CH₃ |
| 31 | phenyl | CH₃ | CH₃ |
| 32 | CH₃ | H | CH₃ |
| 33 | CH₃ | C₂H₅ | CH₃ |
| 34 | CH₃ | n-C₃H₇ | CH₃ |
| 35 | CH₃ | i-C₃H₇ | CH₃ |
| 36 | CH₃ | cyclopropyl | CH₃ |
| 37 | CH₃ | pyrid-2-yl | CH₃ |
| 38 | CH₃ | pyrid-3-yl | CH₃ |
| 39 | CH₃ | pyrid-4-yl | CH₃ |
| 40 | CH₃ | 3-CH₃-isoxazol-5-yl | CH₃ |
| 41 | CH₃ | phenyl | CH₃ |

TABLE C

| No. | R² | R³ | Rᵈ | Rᵉ |
|---|---|---|---|---|
| 1 | H | CH₃ | CH₃ | CH₃ |
| 2 | CH₃ | CH₃ | CH₃ | CH₃ |
| 3 | C₂H₅ | CH₃ | CH₃ | CH₃ |
| 4 | n-C₃H₇ | CH₃ | CH₃ | CH₃ |
| 5 | i-C₃H₇ | CH₃ | CH₃ | CH₃ |
| 6 | cyclopropyl | CH₃ | CH₃ | CH₃ |
| 7 | pyrid-2-yl | CH₃ | CH₃ | CH₃ |
| 8 | pyrid-3-yl | CH₃ | CH₃ | CH₃ |
| 9 | pyrid-4-yl | CH₃ | CH₃ | CH₃ |
| 10 | 5-CH₃-isoxazol-3-yl | CH₃ | CH₃ | CH₃ |
| 11 | phenyl | CH₃ | CH₃ | CH₃ |
| 12 | CH₃ | H | CH₃ | CH₃ |
| 13 | CH₃ | C₂H₅ | CH₃ | CH₃ |
| 14 | CH₃ | n-C₃H₇ | CH₃ | CH₃ |
| 15 | CH₃ | i-C₃H₇ | CH₃ | CH₃ |
| 16 | CH₃ | cyclopropyl | CH₃ | CH₃ |
| 17 | CH₃ | pyrid-2-yl | CH₃ | CH₃ |
| 18 | CH₃ | pyrid-3-yl | CH₃ | CH₃ |
| 19 | CH₃ | pyrid-4-yl | CH₃ | CH₃ |
| 20 | CH₃ | 3-CH₃-isoxazol-5-yl | CH₃ | CH₃ |
| 21 | CH₃ | CH₃ | H | CH₃ |
| 22 | H | CH₃ | C₂H₅ | CH₃ |
| 23 | CH₃ | CH₃ | n-C₃H₇ | CH₃ |
| 24 | C₂H₅ | CH₃ | i-C₃H₇ | CH₃ |
| 25 | n-C₃H₇ | CH₃ | cyclopropyl | CH₃ |
| 26 | i-C₃H₇ | CH₃ | pyrid-2-yl | CH₃ |
| 27 | cyclopropyl | CH₃ | pyrid-3-yl | CH₃ |
| 28 | pyrid-2-yl | CH₃ | pyrid-4-yl | CH₃ |
| 29 | pyrid-3-yl | CH₃ | 3-CH₃-isoxazol-5-yl | CH₃ |
| 30 | CH₃ | CH₃ | CH₃ | C₂H₅ |
| 31 | CH₃ | CH₃ | CH₃ | n-C₃H₇ |
| 32 | CH₃ | CH₃ | CH₃ | i-C₃H₇ |
| 33 | CH₃ | CH₃ | CH₃ | t-C₄H₉ |
| 34 | CH₃ | CH₃ | CH₃ | benzyl |
| 35 | CH₃ | CH₃ | CH₃ | propargyl |
| 36 | CH₃ | CH₃ | CH₃ | bromopropargyl |
| 37 | CH₃ | CH₃ | CH₃ | iodopropargyl |
| 38 | CH₃ | CH₃ | CH₃ | allyl |
| 39 | CH₃ | CH₃ | CH₃ | trans-chloroallyl |
| 40 | CH₃ | CH₃ | CH₃ | CH₃—O—CH₂—CH₂ |

The compounds I listed in Table D are also particularly preferred.

TABLE D

Compounds of the formula

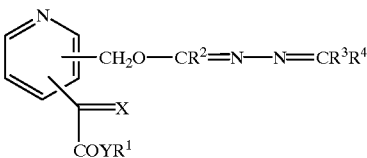

| No. | Position of group CXCOYR$^1$ | X | Y | R$^1$ | Position of group —CH$_2$O—CR$^2$=n-N=CR$^3$R$^4$ | R$^2$ | R$^3$ | R$^4$ |
|---|---|---|---|---|---|---|---|---|
| 1 | 2 | NOCH$_3$ | O | CH$_3$ | 3 | CH$_3$ | CH$_3$ | phenyl |
| 2 | 2 | CHCH$_3$ | O | CH$_3$ | 3 | CH$_3$ | CH$_3$ | phenyl |
| 3 | 2 | CHOCH$_3$ | O | CH$_3$ | 3 | CH$_3$ | CH$_3$ | phenyl |
| 4 | 2 | NOCH$_3$ | NH | CH$_3$ | 3 | CH$_3$ | CH$_3$ | phenyl |
| 5 | 2 | NOCH$_3$ | O | CH$_3$ | 3 | CH$_3$ | CH$_3$ | C(CH$_3$)—C(=NOCH$_3$)-phenyl |
| 6 | 2 | CHCH$_3$ | O | CH$_3$ | 3 | CH$_3$ | CH$_3$ | C(CH$_3$)—C(=NOCH$_3$)-phenyl |
| 7 | 2 | COOCH$_3$ | O | CH$_3$ | 3 | CH$_3$ | CH$_3$ | C(CH$_3$)—C(=NOCH$_3$)-phenyl |
| 8 | 2 | NOCH$_3$ | NH | CH$_3$ | 3 | CH$_3$ | CH$_3$ | C(CH$_3$)—C(=NOCH$_3$)-phenyl |
| 9 | 3 | NOCH$_3$ | O | CH$_3$ | 4 | CH$_3$ | CH$_3$ | phenyl |
| 10 | 3 | CHCH$_3$ | O | CH$_3$ | 4 | CH$_3$ | CH$_3$ | phenyl |
| 11 | 3 | COOCH$_3$ | O | CH$_3$ | 4 | CH$_3$ | CH$_3$ | phenyl |
| 12 | 3 | NOCH$_3$ | NH | CH$_3$ | 4 | CH$_3$ | CH$_3$ | phenyl |
| 13 | 3 | NOCH$_3$ | O | CH$_3$ | 4 | CH$_3$ | CH$_3$ | C(CH$_3$)—C(=NOCH$_3$)-phenyl |
| 14 | 3 | CHCH$_3$ | O | CH$_3$ | 4 | CH$_3$ | CH$_3$ | C(CH$_3$)—C(=NOCH$_3$)-phenyl |
| 15 | 3 | CHOCH$_3$ | O | CH$_3$ | 4 | CH$_3$ | CH$_3$ | C(CH$_3$)—C(=NOCH$_3$)-phenyl |
| 16 | 3 | NOCH$_3$ | NH | CH$_3$ | 4 | CH$_3$ | CH$_3$ | C(CH$_3$)—C(=NOCH$_3$)-phenyl |
| 17 | 4 | NOCH$_3$ | O | CH$_3$ | 3 | CH$_3$ | CH$_3$ | phenyl |
| 18 | 4 | CHCH$_3$ | O | CH$_3$ | 3 | CH$_3$ | CH$_3$ | phenyl |
| 19 | 4 | CHOCH$_3$ | O | CH$_3$ | 3 | CH$_3$ | CH$_3$ | phenyl |
| 20 | 4 | NOCH$_3$ | NH | CH$_3$ | 3 | CH$_3$ | CH$_3$ | phenyl |
| 21 | 4 | NOCH$_3$ | O | CH$_3$ | 3 | CH$_3$ | CH$_3$ | C(CH$_3$)—C(=NOCH$_3$)-phenyl |
| 22 | 4 | CHCH$_3$ | O | CH$_3$ | 3 | CH$_3$ | CH$_3$ | C(CH$_3$)—C(=NOCH$_3$)-phenyl |
| 23 | 4 | CHOCH$_3$ | O | CH$_3$ | 3 | CH$_3$ | CH$_3$ | C(CH$_3$)—C(=NOCH$_3$)-phenyl |
| 24 | 4 | NOCH$_3$ | NH | CH$_3$ | 3 | CH$_3$ | CH$_3$ | C(CH$_3$)—C(=NOCH$_3$)-phenyl |

Equally, the present invention relates to intermediates of the formula II

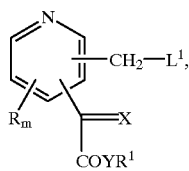

II where R, R$^1$, X, Y and m have the abovementioned meanings and L$^1$ can be a nucleophilically exchangeable leaving group such as, inter alia, halogen, eg. Cl, Br, sulfonate, eg. mesylate, triflate, tosylate, C$_1$–C$_6$-alkoxy as mentioned above, aryloxy as mentioned above and C$_1$–C$_6$-alkylcarbonyloxy as mentioned above. L$^1$ can preferably be chlorine, bromine, mesylate, triflate, methoxy, ethoxy or phenolate (Synthesis, cf. p. 6 et seq. of the present application).

The compounds I are useful as fungicides.

The compounds I are distinguished by an outstanding activity against a broad spectrum of phytopathogenic fungi, in particular from the classes of the Ascomycetes and Basidiomycetes. Some of them act systemically and can be employed as foliar—and soil-acting fungicides.

They are of particular importance for controlling a large number of fungi in a variety of crop plants such as wheat, rye, barley, oats, rice, maize, grass, cotton, soya, coffee, sugar cane, grapevines, fruit species, ornamentals and vegetable species such as cucumbers, beans and cucurbits, and in the seeds of these plants.

Specifically, they are suitable for controlling the following plant diseases: Erysiphe graminis (powdery mildew) in cereals, Erysiphe cichoracearum and Sphaerotheca fuliginea in cucurbits, Podosphaera leucotricha in apples, Uncinula necator in grapevines. Puccinia species in cereals, Rhizoctonia species in cotton and lawns, Ustilago species in cereals and sugar cane, Venturia inaequalis (scab) in apples, Helminthosporium species in cereals, Septoria nodorum in wheat, Botrytis cinerea (gray mold) in strawberries, grapevines, Cercospora arachidicola in groundnuts, Pseudocercosporella herpotrichoides in wheat, barley, Pyricularia oryzae in rice, Phytophthora infestans in potatoes and tomatoes, Fusarium and Verticillium species in a variety of plants, Plasmopara viticola in grapevines, Alternaria species in vegetables and fruit.

The compounds I are applied by treating the fungi, or the plants, seeds, materials or the soil to be protected against fungal infection, with a fungicidally effective amount of the active ingredients. Application takes place before or after infection of the materials, plants or seeds by the fungi.

They can be converted into the customary formulations, such as solutions, emulsions, suspensions, dusts, powders, pastes and granules. The use form depends on the intended purpose; in any case, it should guarantee fine and uniform solution of the compounds according to the invention. The formulations are prepared in a known manner, for example by extending the active ingredients with solvents and/or carriers, if desired using emulsifiers and dispersants, it also being possible for the organic solvents to be used as auxiliary solvents if water is used as the diluent. Suitable auxiliaries are essentially: solvents such as aromatics (eg.

xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers, such as ground natural minerals (eg. kaolins, clays, talc, chalk) and ground synthetic minerals (eg. highly-disperse silica, silicates); emulsifiers such as non-ionic and anionic emulsifiers (eg. polyoxyethylene fatty alcohol ethers, alkylsulfonates and arylsulfonates) and dispersants such as ligninsulfite waste liquors and methylcellulose.

In general, the fungicidal compositions comprise from 0.1 to 95, preferably 0.5 to 90, % by weight of active ingredient.

Depending on the nature of the desired effect, the rates of application are from 0.01 to 2.0 kg of active ingredient per ha.

In the treatment of seed, amounts of active ingredient of from 0.001 to 0.1 g, preferably 0.01 to 0.05 g, are generally required per kilogram of seed.

In the use form as fungicides, the agent according to the invention can also be present together with other active ingredients, eg. with herbicides, insecticides, growth regulators, fungicides, or else fertilizers. A mixture with fungicides in many cases results in a widened fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl) disulfide;

nitro derivatives, such as dinitro (1-methylheptyl) phenylcrotonate, 2-sec-butyl-4,6-dinitrophenyl-3,3-dimethyl acrylate, 2-sec-butyl-4,6-dinitrophenylisopropyl carbonate, di-isopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2, 4-triazole, 2,3-dicyano-1,4-dithioanthraquinon, 2-thio-1,3-dithiolo[4,5-b]quinoxaline, methyl 1-(butylcarbamoyl)-2-benzimidazolecarbamate, 2-methoxycarbonylaminobenzimidazole, 2-(furyl-(2)) benzimidazole, 2-(thiazolyl-(4))benzimidazole, N-(1,1,2,2-tetrachloroethylthio) tetrahydrophthalimide, N-trichloromethylthiotetrahydrophthalimide, N-trichloromethylthiophthalimide, N-dichlorofluoromethylthio-N', N'-dimethyl-N-phenylsulfuric diamide, 5-ethoxy-3-trichloromethyl-1,2,4-thiadiazole, 2-thiocyanatomethylthiobenzothiazole, 1,4-dichloro-2,5-dimethoxybenzene, 4-(2-chlorophenylhydrazone)-3-methyl-5-isoxazolone, pyridine 2-thio-1-oxide, 8-hydroxyquinoline or its copper salt, 2,3-dihydro-5-carboxanilido-6-methyl-1, 4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-[2,2,2-trichloro-1-(morpholin-4-yl)-1-ethyl]formamide, piperazine-1,4-diylbis(1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1, 2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3, 3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methyl-pyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and a variety of fungicides, such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3, 5-dichlorophenyl)-2,4-dioxo-1,3-oxazolidine, 3-[3,5-dichlorophenyl(5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole.

The compounds of the formula I are furthermore suitable for effectively controlling animal pests from the classes of the insects, arachnids and nematodes. They can be employed as pesticides in crop protection and in the hygiene, stored-product and veterinary sector.

The harmful insects include, from the order of the lepidopterans (Lepidoptera), for example, *Argrotis ypsilon, Argrotis segetum, Alabama argillacea, Anticarsia gemmatalis, Argyresthia conjugella, Autographa gamma, Bupalus piniariu, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpum lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra Brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella,*

*Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Orthiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus, Sitophilus granaria.*

From the order of the dipterans (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterans (Hymenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of the heteropterans (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.*

From the order of the homopterans (Homoptera), for example *Acyrthosiphon onobrychia, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Kalotermes flavicollis, Leucotermes flavipes, Reticulitermes lucifugus, Termes natalensis.*

From the order of the orthopterans (Orthoptera), for example, *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the Arachnoidea, for example, arachnids (Acarina) such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the nematodes, for example, root knot nematodes, eg. *Meloidogyne hapla, Meloidogyne incognita, Meloidogyne javanica,* cyst nematodes, eg. *Globodera rostochiensis, Heterodera avenae, Heterodera glycines, Heterodera Schachtii, Heterodera trifolii,* stem eelworms and foliar nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The active ingredients can be used as such, in the form of their formulations or the use forms prepared therefro, eg. in the form of directly sprayable solutions, powders, suspensions or dispersions, emulsions, oil dispersions, pastes, dusts, materials for spreading, or granules, by means of spraying atomizing, dusting, spreading or pouring. The use forms depend entirely on the intended purposes; in any case they should guarantee the finest possible distribution of the active ingredients according to the invention.

The active ingredient concentrations in the ready-to-use preparations can be varied within substantial ranges.

They are generally at from 0.0001 to 10%, preferably from 0.01 to 1%.

The active ingredients can also be used successfully by the ultra-low-volume method (ULV), it being possible to apply formulations comprising over 95% by weight of active ingredient, or even the active ingredient without additives.

Under open conditions, the rate of application of active ingredient for controlling pests is from 0.1 to 2.0, preferably 0.2 to 1.0 kg/ha.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly plar solvents, eg. dimethylformamide, dimethyl sulfoxide, N-methylpyrrolidone and water.

Aqueous use forms can be prepared from emulsion concentrates pastes or wettable powders (sprayable powders, oil dispersions) by adding water. To prepare emulsions, pastes or oil dispersions, the substances, as such or dissolved in an oil or solvent, can be homogenized in water by means of wetting agent, adhesive, dispersant or emulsifier. Alternatively, concentrates which are suitable for dilution with water may be prepared from active ingredient, wetting agent, adhesive, dispersant or emulsifier and, if desired, solvent or oil.

Suitable surfactants are alkali metal salts, alkaline earth metal salts and ammonium slats of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali and alkaline earth metal salts, salts of sulfated fatty alcohol glycol ethers, condensates of sulfonated naphthalene and naphthalene derivatives with formaldehyde, condensates of naphthalene or naphthalenesulfonic acid with phenol and formaldehyde, polyoxyethylene octylphenol ethers, ethoxylated isooctylphenol, octylphenol, nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powders, materials for spreading and dusts can be prepared by mixing or grinding the active ingredients together with a solid carrier.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

EXAMPLES OF FORMULATIONS ARE

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which have been sprayed onto the surface of this silica gel. This gives a preparation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide to 1 mol of oleic acid N-monoethanolamide, 2 parts by weight of calcium dodecylbenzenesulfonate and 2 parts by weight of the adduct of 40 mol of ethylene oxide to 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide to 1 mol of isooctylphenol and 5 parts by weight of the adduct of 40 mol of ethylene oxide to 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide to 1 mol of issoctylphenol and 10 parts by weight of the adduct ob 40 mol of ethylene oxide to 1 mol of castor oil. Pouring the solution into 100,000 parts by weight of water and finely distributing it therein gives an aqueous dispersion which comprises 0.02% by weight of the active ingredient.

VIII. 20 parts by weight of the compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

Granules, eg. coated granules, impregnated granules and homogeneous granules, can be prepared by binding the active ingredient to solid carriers. Examples of solid carriers are mineral earths such as silica gel, silicas, silica gels, silicates, talc, kaolin, attaclay, limestone, lime, chalk, bole, loes, clay, dolomite, diatomaceous earth, calcium sulfate, magnesium sulfate, magnesium oxide, ground polymers, fertilizers, eg. ammonium sulfate, ammonium phosphate, ammonium nitrate, ureas, and products of vegetable origin, such as cereal meal, tree bark meal, wood meal and nutshell meal, cellulose powders and other solid carriers.

Various types of oils, or herbicides, fungticides, other pesticides and bactericides may be admixed with the active ingredients, if desired also only prior to use (tank mix). These agents can be admixed with the agents according to the invention in a weight ratio of 1:10 to 10:1.

SYNTHESIS EXAMPLES

The protocols given in the Synthesis Examples which follow were also used for obtaining other compounds I by choosing suitable starting compounds. The resulting compounds are listed in the Tables which follow together with physical data.

1. Synthesis of

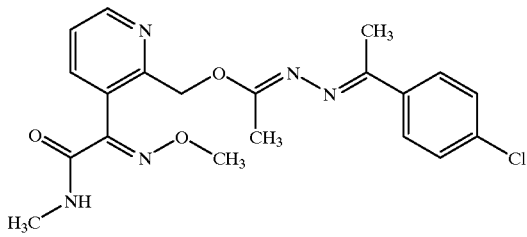

a) 2-Methyl-3-formylpyridine cyanohydrin

A mixture of 33 g (0.5 mol) of KCN and 26 g (0.5 mol) of NH$_4$Cl 200 ml of water and 30 g (0.24 mol) of 2-methyl-3-formylpyridine (Chem. Pharm. Bull. 42 (1994), 1941; J. Med. Chem. 32 (1989), 583; J. Heterocycl. Chem. 28 (1991), 1315; J. Org. Chem. 43 (1978), 324) in 200 ml in diethyl ether was stirred for 2 hours at room temperature, during which process the product crystallized out. The solid was filtered off with suction, washed with methyl t-butyl ether and dried in a stream of nitrogen (yield: 19.3 g (54%); m.p.=139° C.).

$^1$H NMR (DMSO-d$_6$; δ in ppm): 8.5 (d, broad, 1H, pyridyl); 7.9 (d, broad, 1H, pyridyl); 7.3 (dd, 1H, pyridyl); 7.2 (s, broad, 1H, OH); 5.9 (s, 1H, CH); 2.55 (s, 3H, CH$_3$).

b) Methyl (2-methylpyrid-3-yl)-α-hydroxyacetate 15 g (0.4 mol) of gaseous hydrochloric acid were passed into a solution of 22 g (0.15 mol) of 2-methyl-3-formylpyridine cyanohydrin (Example 1a) in 250 ml of methanol. The reaction mixture was stirred overnight at room temperature and subsequently evaporated in vacuo. The residue was taken up in 200 ml of water and refluxed for 1 hour. The reaction mixture was subsequently cooled to room temperature, neutralized with NaHCO$_3$ solution and extracted with methylene chloride. The combined organic phases were dried over MgSO$_4$ and concentrated. The residue was purified by column chromatography using cyclohexane/ethyl acetate mixtures. This gave 3.0 g (11%) of the title compound as a pale oil.

$^1$H NMR (CDCl$_3$; δ in ppm): 8.35 (d, broad, 1H, pyridyl); 7.7 (d, broad, 1H, pyridyl); 7.15 (dd, 1H, pyridyl); 5.4 (s, 1H, CH); 4.5 (s, very broad, 1H, OH); 3.75 (s, 3H, OCH$_3$); 2.6 (s, 3H, CH$_3$).

c) Methyl (2-methylpyrid-3-yl)glyoxylate

A stirred mixture of 3 g (16 mmol) of methyl (2-methylpyrid-3-yl)-α-hydroxyacetate (Example 1b) in 20 ml of methylene chloride and 0.5 g (3.5 mmol) of Na$_2$HPO$_4$, 0.6 g (5 mmol) of NaH$_2$PO$_4$ and 0.2 g (1.6 mmol) of KBr in 20 ml of water was treated with a spatula-tipful of tetramethylpyridine N-oxyl and 10 ml of 12.5% strength sodium hypochlorite solution. The mixture was stirred for 1 hour at room temperature, and the organic phase was subsequently separated off and concentrated. The residue obtained was 2.2 g (77%) of the title compound as a yellow oil.

$^1$H NMR (CDCl$_3$; δ in ppm): 8.7 (d, broad, 1H, pyridyl); 8.05 (d, broad, 1H, pyridyl); 7.3 (dd, 1H, pyridyl); 4.0 (s, 3H, OCH$_3$); 2.8 (s, 3H, CH$_3$).

d) Methyl (2-methylpyrid-3-yl)glyoxylate trans-O-methyloxime

A mixture of 2.2 g (12 mmol) of methyl (2-methylpyrid-3-yl)glyoxylate (Example 1c) and 1.5 g (18 mmol) of O-methylhydroxylamine hydrochloride in 20 mol of methanol were stirred overnight at room temperature. The reaction mixture was subsequently concentrated. The residue was taken up in methylene chloride and extracted with a small amount of water. The organic phase was dried over MgSO$_4$ and concentrated. The residue was purified by column chromatography using cyclohexane/ethyl acetate mixtures. This gave 1.8 g (73%) of the title compound as a pale oil.

$^1$H NMR (CDCl$_3$; δ in ppm): 8.55 (d, broad, 1H, pyridyl); 7.45 (d, broad, 1H, pyridy), 7.2 (dd, 1H, pyridyl); 4.1 (s, 3H, OCH$_3$); 3.9 (s, 3H, OCH$_3$); 2.45 (s, 3H, CH$_3$).

e) Methyl (2-bromomethylpyrid-3-yl)glyoxylate trans-O-methyloxime

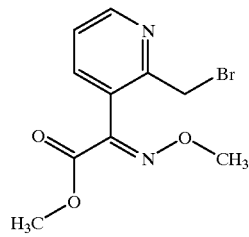

A mixture of 1.8 g (8.7 mmol) of methyl (2-methylpyrid-3-yl)glyoxylate trans-O-methyloxime, 1.7 g (9.6 mmol) of N-bromosuccinimide and a spatula-tipful of azobisisobutyronitrile in 30 ml of CCl$_4$ was irradiated for approximately 4 hours with a 300 W UV lamp, during which process the temperature of the reaction mixture climbed to reflux temperature. The reaction mixture was subsequently diluted with methylene chloride and the organic phase was extracted with water. The organic phase was extracted with water, dried over MgSO$_4$ and concentrated. The residue was purified by column chromatography using cyclohexane/ethyl acetate mixtures. This gave 1.1 g (44%) of the title compound as a pale oil.

$^1$H NMR (CDCl$_3$; δ in ppm): 8.65 (d, board, 1H, pyridyl); 7.55 (d, broad, 1H, pyridyl); 7.3 (t, broad, 1H, pyridyl); 4.4 (s, 2H, CH$_2$Br); 4.1 (s, 3H, OCH$_3$); 3.9 (s, 3H, OCH$_3$).

f) N'-Acetyl-4-chloroacetophenone hydrazone

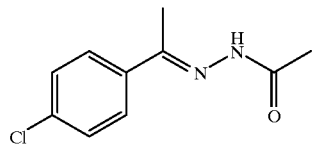

A mixture of 15.5 g (0.1 mol) of 4-chloroacetophenone, 82 g (0.1 mol) of N-acetylhydrazide and a drop of concentrated hydrochloric acid in 100 ml of methanol was heated for 3 hours at 40–50° C. During this process, the product crystallized out. The reaction mixture was cooled, and the solid which had crystallized out was filtered off, washed with methanol/methyl t-butyl ether and dried in a stream of air. This gave 16 g (76%) of the title compound as a colorless solid (m.p.=170–172° C.).

$^1$H NMR (CDCl$_3$; δ in ppm): 9.75 (s, 1H, NH); 7.7 (d, 2H, phenyl); 7.35 (d, 2H, phenyl); 2.4 (s, 3H, CH$_3$); 2.3 (s, 3H, CH$_3$).

g) Synthesis of

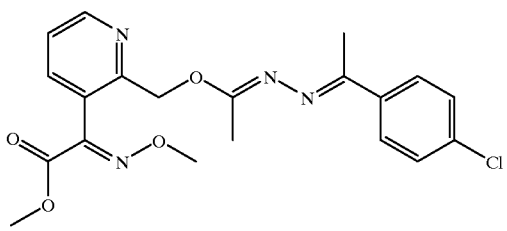

A mixture of 1.5 g (7 mmol) of N'-acetyl-4-chloroacetophenone hydrazone (Example 1f) and 0.2 g (8 mmol) of sodium hydride in 20 ml of dimethylformamide was stirred for 15 minutes at room temperature. 2 g (7 mmol) of methyl (2-bromomethylpyrid-3-yl)glyoxylate trans-O-methyloxime (Example 1e) and 0.1 g of sodium iodide were subsequently added and the mixture was stirred for 2 hours at room temperature. The reaction mixture was then diluted with water and the aqueous phase was extracted three times with methyl t-butyl ether. The combined organic phases were dried over $MgSO_4$ and concentrated. The residue was purified by column chromatography using cyclohexane/ethyl acetate mixtures. This gave 1.1 g (38%) of the title compound as pale yellow crystals (m.p.=113–114° C.).

$^1$H NMR ($CDCl_3$; δ in ppm): 8.65 (dd, 1H, pyridyl); 7.75 (d, 2H, phenyl); 7.6 (broad, 1H, pyridyl); 7.35 (m, 3H, 2×phenyl, 1×pyridyl); 5.3 (s, 2H, $OCH_2$); 4.05 (s, 3H, $OCH_3$); 3.9 (s, 3H, $OCH_3$); 2.2 (s, 3H, $CH_3$); 2.1 (s, 3H, $CH_3$).

h) Synthesis of

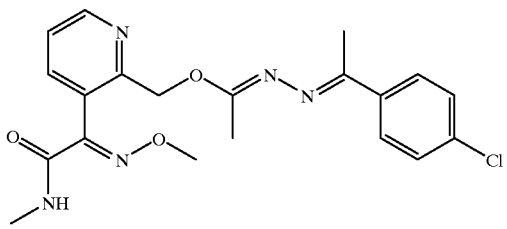

A mixture of 0.5 g (1.2 mmol) of the ester of Example 1g, 5 ml of tetrahydrofuran and 20 ml of 40% strength methylamine solution was stirred for 1 hour at room temperature. The reaction mixture was subsequently concentrated in vacuo and the residue was purified by column chromatography using cyclohexane/ethyl acetate mixtures. This gave 0.45 g (90%) of the title compound as a yellow oil.

$^1$H NMR ($CDCl_3$; δ in ppm): 8.65 (d, broad, 1H, pyridyl); 7.75 (d, 2H, phenyl); 7.6 (d, broad, 1H, pyridyl); 7.35 (m, 3H, 2×phenyl, 1×pyridyl); 6.85 (s, very broad, 1H, NH); 5.3 (s, 2H, $OCH_2$); 3.95 (s, 3H, $OCH_3$); 2.9 (d, 3H, $NCH_3$); 2.2 (s, 3H, $CH_3$); 2.1 (s, 3H, $CH_3$).

The compounds listed in Table E were synthesized by similar methods.

TABLE E

Physical data of some selected compounds

| No. | Formula | $R^2$ | $R^3$ | $R^4$ | $R^d$ | $R^e$ | M.p. [° C.] or $^1$H NMR [ppm] |
|---|---|---|---|---|---|---|---|
| E.1 | IA.1 | $CH_3$ | $CH_3$ | 4-Cl-phenyl | — | — | 113–114 |
| E.2 | IB.1 | $CH_3$ | $CH_3$ | 4-Cl-phenyl | — | — | 3.95(s, 3H); 2.9(d, 3H) |
| E.3 | IA.1.1 | $CH_3$ | $CH_3$ | — | 4-Cl-phenyl | $CH_3$ | 90–95 |
| E.4 | IB.1.1 | $CH_3$ | $CH_3$ | — | 4-Cl-phenyl | $CH_3$ | 138–141 |

Examples of the Activity Against Harmful Fungi

The fungicidal activity of the compounds of the formula I was demonstrated by the following experiments:

The active ingredients were formulated as a 10% emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Emulphor® EL (Emulan® EL, emulsifier based on ethoxylated fatty alcohols) and diluted with water to give the desired concentration.

Activity against powdery mildew of wheat (*Erysiphe graminis* var. *tritici*)

Leaves of wheat seedlings (cultivar "Frühgold") grown in pots were sprayed with a spray mixture comprising 80% of active ingredient and 20% of emulsifier in the dry matter and, 24 hours after the treatment, dusted with oidia (spores) of powdery mildew of wheat (*Erisyphe graminis* var. *triciti*). The test plants were subsequently placed in a greenhouse at from 20 to 22° C. and a relative atmospheric humidity of 75 to 80%. The extent of mildew developement was determined after 7 days.

| Compound | % infection of the leaves after application of a preparation comprising 250 ppm of active ingredient |
|---|---|
| E.2 | 25 |
| E.4 | 25 |
| Untreated | 70 |

Examples of the Activity Against Animal Pests

The activity of the compounds of the general formula I against animal pests was demonstrated by the following experiments:

The active ingredients were formulated
a) as a 0.1% strength solution in acetone or
b) as a 10% emulsion in a mixture of 70 parts by weight of cyclohexanone, 20 parts by weight of Nekanil® LN (Lutensol® AP6, wetting agent having emulsifying and dispersant action based on ethoxylated alkylphenols) and 10% by weight of Emulphor® EL (Emulan®EL, emulsifier based on ethoxylated fatty alcohols)
and diluted to give the desired concentration, using acetone in the case of a) and water in the case of b).

After the experiments had ended, the lowest concentration was determined in each case at which the compounds still caused an 80–100% inhibition or mortality in comparison with untreated controls (limit or minimal concentration).

We claim:

1. A pyridylacetic acid compound of the formula I

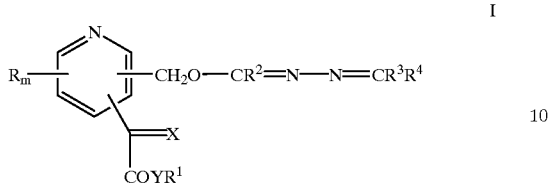

where m and the substituents have the following meanings:

X is $NOCH_3$, $CHOCH_3$ and $CHCH_3$;

Y is oxygen or $NR^a$;

$R^a$ is hydrogen or $C_1$–$C_4$-alkyl;

R is cyano, nitro, trifluoromethyl, halogen, $C_1$–$C_4$-alkyl and $C_1$–$C_4$-alkoxy;

m is 0, 1 or 2, it being possible for these radicals to be different when m is 2;

$R^1$ is hydrogen or $C_1$–$C_4$-alkyl;

$R^2$ and $R^3$ idependently of one another are hydrogen, cyano, nitro, hydroxyl, amino, halogen, $C_1$–$C_6$-alkyl, $C_1$–$C_6$-alkoxy, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_2$–$C_6$-alkenylthio, $C_2$–$C_6$-alkenylamino, N-$C_2$–$C_6$-alkenyl-N-$C_1$–$C_6$-alkylamino, $C_2$–$C_6$-alkynyl, $C_2$–$C_6$-alkynyloxy, $C_2$–$C_6$-alkynylthio, $C_2$–$C_6$-alkynylamino, N-$C_2$–$C_6$-alkynyl-N-$C_1$–$C_6$-alkylamino, it being possible for the hydrocarbon radicals of these groups to be partially or fully halogenated or to have attached to them one to three of the following radicals: cyano, nitro, hydroxyl, mercapto, amino, carboxyl, aminocarbonyl, aminothiocarbonyl, halogen, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyul, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_2$–$C_6$-alkylamino, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, aryl-$C_1$–$C_4$-alkoxy, arylthio, aryl-$C_1$–$C_4$-alkylthio, hetaryl, hetaryloxy, hetaryl-$C_1$–$C_4$-alkoxy, hetarylthio, hetaryl-$C_1$–$C_4$-alkylthio, it being possible for the cyclic radicals, in turn, to be partially or fully halogenated and to have attached to them one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and C(=$NOR^b$)—$A_n$—$R^c$;

$C_3$–$C_6$-cycloalkyl, $C_3$–$C_6$-cycloalkyloxy, $C_3$–$C_6$-cycloalkylthio, $C_3$–$C_6$-cycloalkylamino, N-$C_3$–$C_6$-cycloalkylN-$C_1$–$C_6$-alkylamino, $C_3$–$C_6$-cycloalkenyl, $C_3$–$C_6$-cycloalkenyloxy, $C_3$–$C_6$-cycloalkenylthio, $C_3$–$C_6$-cycloalkenylamino, N-$C_3$–$C_6$-cycloalkenyl-N-$C_1$–$C_6$-alkylamino, heterocyclyl, heterocyclyloxy, heterocyclylthio, heterocyclylamino, N-heterocyclyl-N-$C_1$–$C_6$-alkylamino, aryl, aryloxy, arylthio, arylamino, N-aryl-N-$C_1$–$C_6$-alkylamino, hetaryl, hetaryloxy, hetarylthio, hetarylamino, N-hetaryl-N-$C_1$–$C_6$-alkylamino, it being possible for the cyclic radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkoxy-$C_1$–$C_6$-alkyl, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, aryl-$C_1$–$C_6$-alkoxy, hetaryl, hetaryloxy, it being possible for the cyclic radicals of the seven last-mentioned substituents to be partially or fully halogenated and to have attached to them a $C_1$–$C_6$-alkyl group; C(=$NOR^b$)—$A_n$—$R^c$ or $NR^f$—CO—D—$R^g$;

A is oxygen, sulfur or nitrogen, the nitrogen having attached to it hydrogen or $C_1$–$C_6$-alkyl;

D is a direct bond, oxygen or $NR^h$;

n is 0 or 1;

$R^b$, $R^c$ idenpendently of one another are hydrogen or $C_1$–$C_6$-alkyl;

$R^f$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy and $C_1$–$C_6$-alkoxycarbonyl;

$R^g$, $R^h$ independently of one another are hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl;

$R^4$ is one of the groups metnioned under $R^2$ or a group $CR^d$=$NOR^e$;

$R^d$ is one of the groups mentioned under $R^2$;

$R^e$ is hydrogen, $C_1$–$C_{10}$-alkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_3$–$C_{10}$-alkynylcarbonyl or $C_1$–$C_{10}$-alkylsulfonyl, it being possible for these radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, $C_3$–$C_6$-cycloalkyl, $C_3$–$C_6$-cycloalkoxy, heterocyclyl, heterocyclyloxy, benzyl, benzyloxy, aryl, aryloxy, arylthio, hetaryl, hetaryloxy and hetarylthio, it being possible for the twelve last mentioned groups, in turn, to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$- alkyl, $C_1$–$C_6$-haloalkyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, hetaryl, hetaryloxy, hetarylthio and $C(=NOR^b)$—$A_n$—$R^c$;

$C_3$–$C_6$-cycloalkyl, aryl, arlycarbonyl, arylsulfonyl, hetaryl, hetarylcarbonyl or hetarylsulfonyl, it being possible for these radicals to be partially or fully halogenated or to have attached to them one to three of the following groups: cyano, nitro, hydroxyl, mercapto, amino, carboxyl, aminocarbonyl, aminothiocarbonyl, halogen, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy, $C(=NOR^b)$—$A_n$—$R^c$ or $NR^f$—CO—D—$R^g$;

or a salt thereof.

2. The compound of the formula I defined in claim 1 where X is $NOCH_3$ and Y is $NR^a$.

3. The compound of the formula I defined in claim 1 where m is 0.

4. The compound of the formula I defined in claim 1 where $R^1$ is methyl.

5. A process for the preparation of a compound I defined in claim 1 where $R^2$ is not halogen, which comprises reacting a compound of the formula II

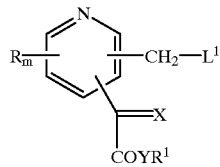

where $L^1$ is a nucleophilically exchangeable leaving group with a carbohydrazide of the formula III

6. A process for the preparation of a compound I defined in claim 1 where Y is $NR^a$, which comprises reacting a pyridylacetic acid ester of the formula Ia

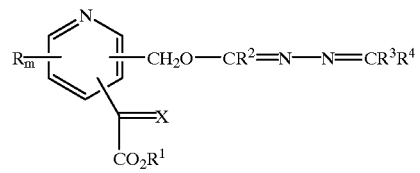

with an amine of the formula VI

7. An intermediate of the formula II

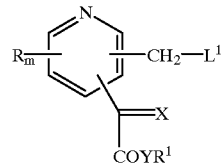

where $L^1$ is a nucleophilically exchangeable leaving group;

X is $NOCH_3$, $CHOCH_3$ and $CHCH_3$;

Y is oxygen or $NR^a$;

$R^a$ is hydrogen or $C_1$–$C_4$-alkyl;

R is cyano, nitro, trifluoromethyl, halogen, $C_1$–$C_4$-alkyl and $C_1$–$C_4$-alkoxy;

m is 0, 1 or 2, it being possible for these radicals to be different when m is 2;

$R^1$ is hydrogen or $C_1$–$C_4$-alkyl.

8. A compossition suitable for controlling pests or harmful fungi, comprising a solid or liquid carrier and an effective amount of a compound of the formula I as defined in claim 1.

9. A method of controlling harmful fungi, which comprises treating the fungi, or the materials, plants, the soil or seed to be protectes against fungal infection, with an effective amount of a compound of the formula I as defined in claim 1.

10. A method of controlling pests, which comprises treating the pests, or the materials, plants, the soil or seed to be protected against said pests, with an effective amount of a compound of the formula I as defined in claim 1.

* * * * *

UNITED STATES PATENT AND TRADEMARK OFFICE
CERTIFICATE OF CORRECTION

PATENT NO.: 6,043,197
DATED: March 28, 2000
INVENTOR(S): MÜLLER et al.

It is certified that error appears in the above-identified patent and that said Letters Patent is hereby corrected as shown below:

IN THE CLAIMS

Column 43, claim 1, line 41, change "alkylsulfonyul" to --alkylsulfonyl--.

Column 43, claim 1, line 43, change "di-$C_2$-$C_6$" to -- di-$C_1$-$C_6$--.

Column 44, claim 1, line 42, change "metnioned" to --mentioned-.

Signed and Sealed this

Twenty-seventh Day of March, 2001

*Attest:*

NICHOLAS P. GODICI

*Attesting Officer*  Acting Director of the United States Patent and Trademark Office

UNITED STATES PATENT AND TRADEMARK OFFICE
CERTIFICATE OF CORRECTION

PATENT NO. : 6,043,197
DATED : March 28, 2000
INVENTOR(S) : Mueller et al.

It is certified that error appears in the above-identified patent and that said Letters Patent is hereby corrected as shown below:

Column 44, claim 1,
Line 30, "idenpendently" should be -- independently --.

Column 46, claim 9,
Line 46, "protects" should be -- protected --.

Signed and Sealed this

Twentieth Day of November, 2001

Attest:

*Nicholas P. Godici*

NICHOLAS P. GODICI
*Attesting Officer*   *Acting Director of the United States Patent and Trademark Office*